US009659788B2

(12) United States Patent
Surla et al.

(10) Patent No.: US 9,659,788 B2
(45) Date of Patent: May 23, 2017

(54) NITROGEN-CONTAINING COMPOUNDS FOR ETCHING SEMICONDUCTOR STRUCTURES

(71) Applicant: American Air Liquide, Inc., Fremont, CA (US)

(72) Inventors: Vijay Surla, Newark, DE (US); Rahul Gupta, Newark, DE (US); Venkateswara R. Pallem, Hockessin, DE (US)

(73) Assignee: American Air Liquide, Inc., Fremont, CA (US)

( * ) Notice: Subject to any disclaimer, the term of this patent is extended or adjusted under 35 U.S.C. 154(b) by 0 days.

(21) Appl. No.: 14/841,271

(22) Filed: Aug. 31, 2015

(65) Prior Publication Data

US 2015/0371869 A1 Dec. 24, 2015

(51) Int. Cl.
*H01L 21/311* (2006.01)
*C07C 255/10* (2006.01)
*C07C 251/08* (2006.01)
*C07C 251/26* (2006.01)

(52) U.S. Cl.
CPC ...... *H01L 21/31116* (2013.01); *C07C 251/08* (2013.01); *C07C 251/26* (2013.01); *C07C 255/10* (2013.01); *H01L 21/31144* (2013.01)

(58) Field of Classification Search
CPC .............. C23C 16/45544; C23C 16/52; H01L 21/68764; H01L 21/68771
See application file for complete search history.

(56) References Cited

U.S. PATENT DOCUMENTS

| | | | |
|---|---|---|---|
| 3,585,218 A * | 6/1971 | Balbott | C07C 409/04 149/119 |
| 3,671,509 A | 6/1972 | Howard | |
| 2006/0062914 A1* | 3/2006 | Garg | C03C 15/00 427/248.1 |
| 2010/0105595 A1 | 4/2010 | Lee | |
| 2014/0012033 A1* | 1/2014 | Buisine | C07C 253/14 558/308 |

FOREIGN PATENT DOCUMENTS

EP 1 691 410 8/2006

OTHER PUBLICATIONS

International Search Report and Written Opinion for corresponding PCT/US2016/049479, Nov. 2, 2016.

* cited by examiner

*Primary Examiner* — Duy Deo
(74) *Attorney, Agent, or Firm* — Patricia E. McQueeney; Yan Jiang

(57) ABSTRACT

A method for etching silicon-containing films is disclosed. The method includes the steps of introducing a vapor of a nitrogen containing etching compound into a reaction chamber containing a silicon-containing film on a substrate, wherein the nitrogen containing etching compound is an organofluorine compound containing at least one C=N or C≡N functional group; introducing an inert gas into the reaction chamber; and activating a plasma to produce an activated nitrogen containing etching compound capable of etching the silicon-containing film from the substrate.

20 Claims, 28 Drawing Sheets

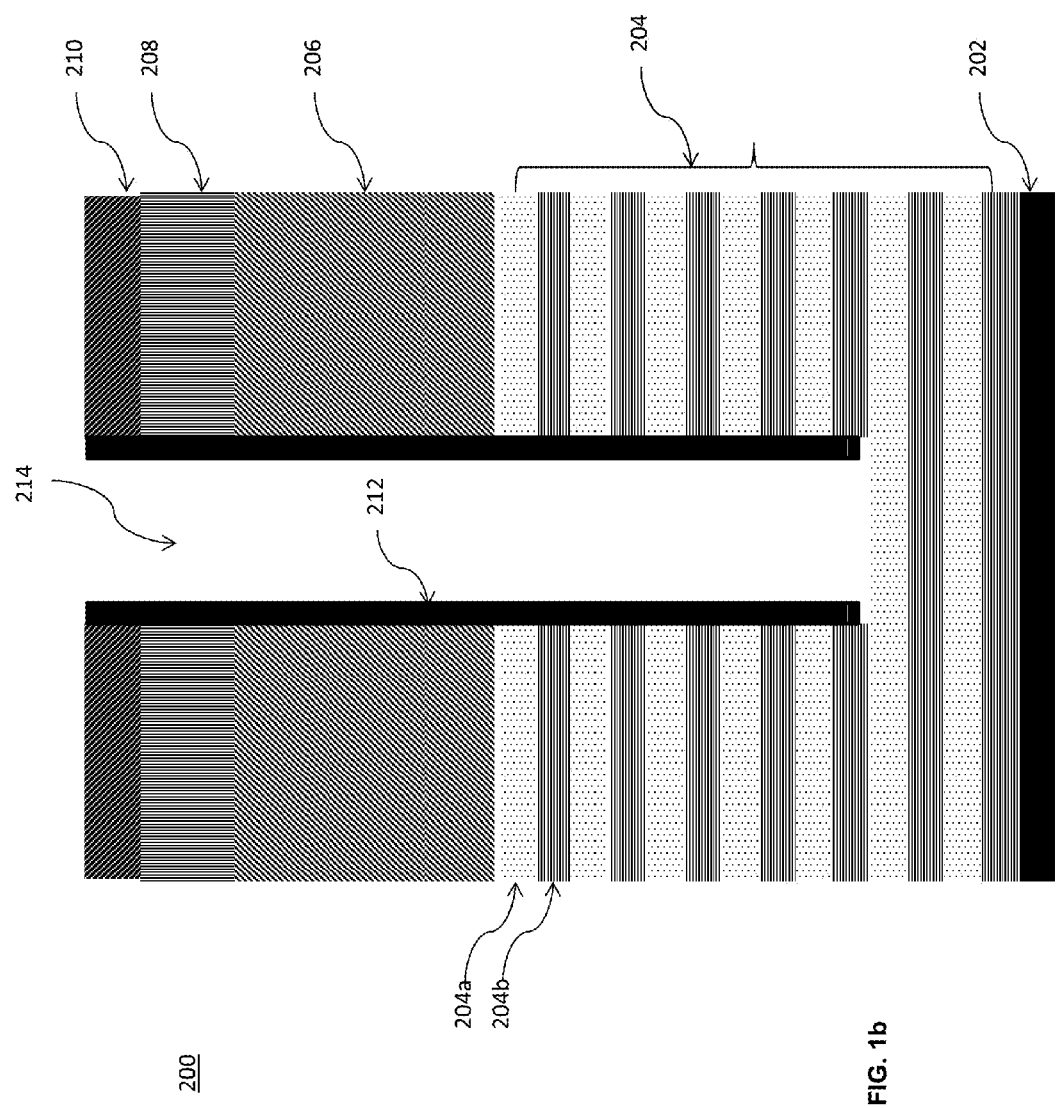

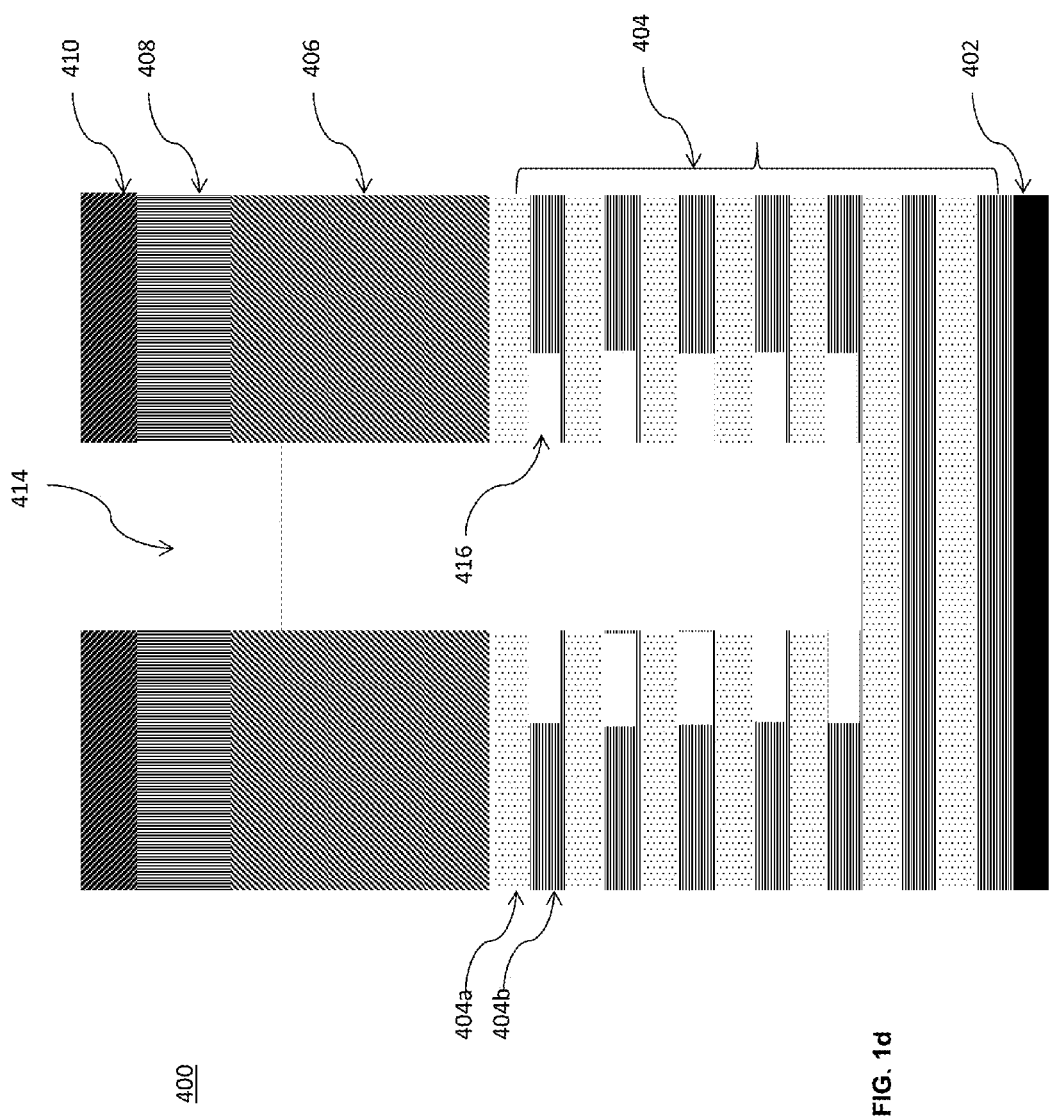

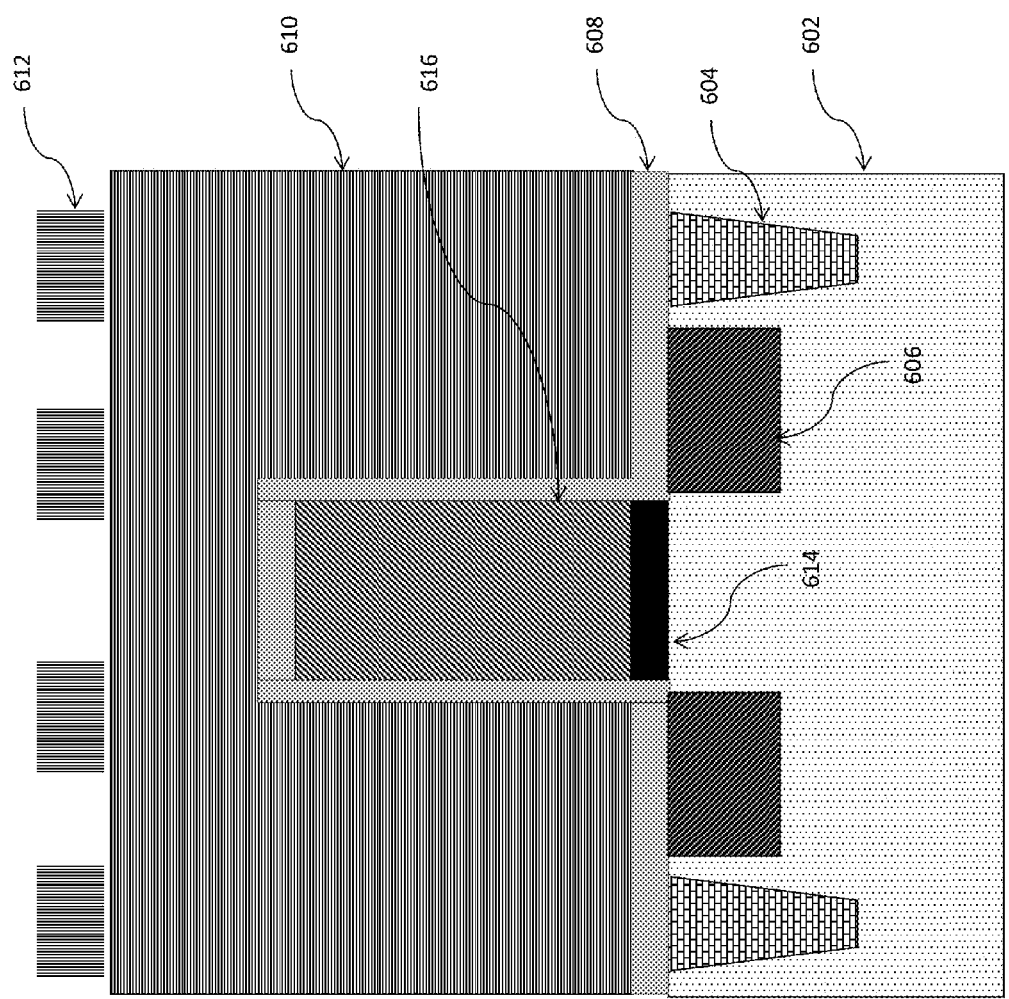

NITROGEN-CONTAINING COMPOUNDS FOR ETCHING SEMICONDUCTOR STRUCTURES

TECHNICAL FIELD

Disclosed are nitrogen-containing etching compounds for plasma etching of silicon-containing films on a substrate and plasma etching methods of using the same. The disclosed nitrogen-containing organofluorine etching gases obtain high etch selectivity in semiconductor device etch applications.

BACKGROUND

In memory applications in the semiconductor industries, such as DRAM and 2D NAND, plasma etching removes silicon-containing films, such as SiO or SiN layers, from semiconductor substrates. For novel memory applications, such as 3D NAND (e.g., see US 2011/0180941 to Samsung Electronics Co., Ltd.), etching of stacks of multiple SiO/SiN or SiO/poly-Silicon (p-Si) layers is critical. An etchant having high selectivity between a mask and the layers being etched is an essential. Furthermore, an etched structure etched by the etchant on the stacks of multiple SiO/SiN or SiO/p-Si layers should have a straight vertical profile without bowing.

Traditional etch gases include octafluorocyclobutane ($cC_4F_8$), hexafluoro-1,3-butadiene ($C_4F_6$), $CF_4$, $CH_2F_2$, $CH_3F$, and/or $CHF_3$. It is well known that selectivity and polymer deposition rate increase as the ratio of C:F increases (i.e., $C_4F_6 > C_4F_8 > CF_4$). See, e.g., U.S. Pat. No. 6,387,287 to Hung et al.

However, traditional etch chemistries may not provide higher aspect ratio than 20:1 necessary in new applications (e.g., 3D NAND) at least due to insufficient etch resistant polymer deposition on sidewalls during plasma etching processes. Here, 20:1 refers to a ratio of the height of a trench (or via) to the width of the trench (or the diameter of the via) being etched. Additionally, $—C_xF_y—$, wherein x ranges from 0.01 to 1 and y ranges from 0.01 to 4, polymers on sidewalls are susceptible to etching. As a result, the etched patterns may not be vertical and the etch structures may show bowing, change in dimensions, and/or pattern collapse.

Bowing may result from sidewall etching of the mask layer, which may often be an amorphous carbon (a-C) material. The a-C materials may be etched by oxygen radicals in the plasma which may cause increased opening of the mask and result in bow-like, or angled/curved, etch structures.

Ji et al. (U.S. Pat. No. 5,814,563) disclose using a mixture of fluorohydrocarbon, carbon-oxygen, and $NH_3$-generating gases to achieve high selectivity of dielectric (such as SiO and SiN) to p-Si layers. Shane (US 2003/0162395) discloses addition of nitrogen-comprising gas to fluorocarbon to deposit polymer on mask to improve selectivity while etching silicon dioxide layer. Nemani et al. (US 2014/0199851) disclose using a plasma process performed by flowing $NF_3$ and $NH_3$ to remove the modified portion of silicon nitride layer to pattern a silicon nitride dielectric film. Hamrah et al. (U.S. Pat. No. 5,242,538) discloses using $CF_4$ and $NH_3$ etching gases and selectivity of silicon oxide to polysilicon selectivity of up to 100:1 was observed. Pu et al. (U.S. Pat. No. 5,843,847) also discloses adding additional nitrogen gas to fluorinated etching gas to assist in feature dimensional control.

Nitrogen containing compounds have been used as etching gases. For example, Khandelwal, et al. ("Dry removal technology for advanced CMOS devices", Nanochip Tech. J., vol. 11, issue 2, 2013, p 17-19) disclose an in-situ dry removal process using $NH_4F$ as etchant. Garg et al. (US 2006/0062914) disclose an activated reactive gas to treat the surface of a substrate. Garg et al. describe at paragraph [0019] that the activated reactive gas may include a large variety of fluorine-containing gases, including $C_3F_3N_3$, fluoroamines such as $CF_5N$, fluoronitriles such as $C_2F_3N$, $C_3F_6N$, and $CF_3NO$. Felker et al. (U.S. Pat. No. 6,508,948) disclose perfluorinated heteroaromatic amine etching compounds, including cyanuric fluoride compounds. One disclosed cyanuric fluoride compound is pentafluoropyridine $C_5F_5N$.

It is important to minimize bowing and to achieve high aspect ratio (i.e., up to 200:1) needed for current applications (e.g., contact etch or 3D NAND). Additionally, etching today has not been limited to selectivity to the photoresist mask. It is equally important to get high selectivity among other materials such as a-C, SiN, p-Si, SiC or other forms of $Si_aC_bO_cH_dN_e$ materials (where a>0; b, c, d and e≥0).

Thus, a need remains for new etch gas compositions for use in plasma etching applications, which may maintain selectivity and high aspect ratio for a wide range of process conditions.

SUMMARY

Disclosed are methods for plasma etching silicon-containing films. The methods include the steps of: introducing a vapor of a nitrogen containing etching compound into a reaction chamber containing a silicon-containing film on a substrate, wherein the nitrogen containing etching compound comprises an organofluorine compound containing a C≡N or C═N functional group; introducing an inert gas into the reaction chamber; and activating a plasma to produce an activated nitrogen containing etching compound capable of etching the silicon-containing film from the substrate. The disclosed methods may include one or more of the following aspects:

- the organofluorine compound containing a C≡N functional group;
- the organofluorine compound having the formula N≡C—$R^1$, wherein $R^1$ has the formula $H_aF_bC_c$ and a=0, b=1-11, and c=1-5;
- the organofluorine compound being trifluoroacetonitrile ($C_2F_3N$) having the formula

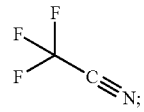

- the organofluorine compound being nonafluoropentanitrile ($C_5F_9N$) having the formula

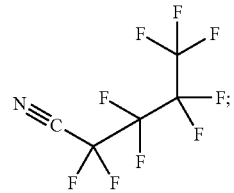 [SMILES: N#CC(F)(F)C(F)(F)C(F)(F)C(F)(F)F]

the organofluorine compound being pentafluoroallyl cyanide ($C_4F_5N$) having the formula

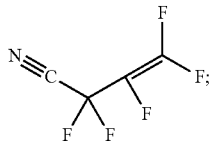

the organofluorine compound having the formula $N\equiv C-R^1$, wherein $R^1$ has the formula $H_aF_bC_c$ and a=1-11, b=1-11, and c=1-5;

the organofluorine compound being difluoroacetonitrile ($C_2HF_2N$) having the formula

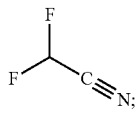

the organofluorine compound being 2,3,3,3-tetrafluoropropionitrile ($C_3HF_4N$) having the formula

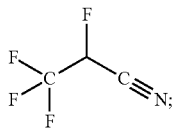

the organofluorine compound being 2,2,3,3-tetrafluoropropionitrile ($C_3HF_4N$) having the formula

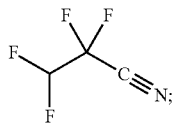

the organofluorine compound being 4,4,4-Trifluorocrotono-nitrile ($C_4H_2F_3N$) having the formula

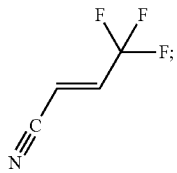

the organofluorine compound being 3,3,3-Trifluoropropionitrile ($C_3H_2F_3N$) having the formula

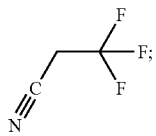

the organofluorine compound being fluoroacetonitrile ($C_2H_2FN$) having the formula

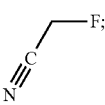

the organofluorine compound having the formula ($N\equiv C-)-(R^1)-(-C\equiv N$), wherein each $R^1$ independently has the formula $H_aF_bC_c$ with a=0, b=1-11, and c=1-5;

the organofluorine compound being octafluorohexane-1,6-dinitrile ($C_6F_8N_2$) having the formula

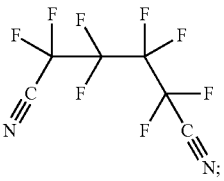 [SMILES: N#CC(F)(F)C(F)(F)C(F)(F)C(F)(F)C#N]

the organofluorine compound being 1,1-bis(trifluoromethyl)-2,2-dicyanoethylene ($C_6F_6N_2$) having the formula

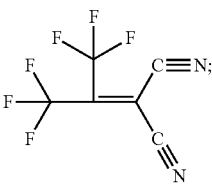 [SMILES: N#CC(C#N)=C(C(F)(F)F)C(F)(F)F]

the organofluorine compound having the formula ($N\equiv C-)-(R^1)-(-C\equiv N$), wherein each $R^1$ independently has the formula $H_aF_bC_c$ with a=1-11, b=1-11, and c=1-5;

the organofluorine compound being 2-[1-(difluoromethyl)-2,2,2-trifluoroethylidene]-propanedinitrile ($C_6HF_5N_2$) having the formula

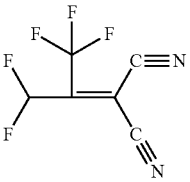

the organofluorine compound containing a $C\equiv N$ functional group;

the organofluorine compound having the formula $R^1_x[-C\equiv N(R^2_z)]_y$, wherein x=1-2, y=1-2, z=0-1, x+z=1-3, and each $R^1$ and $R^2$ independently has the formula $H_aF_bC_c$ with a=0, b=1-11, and c=0-5;

the organofluorine compound being N,1,1,1,3,3,3-heptafluoro-propanamine ($C_3F_7N$) having the formula

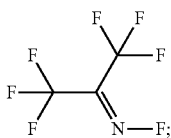

the organofluorine compound having the formula $R^1_x[-C=N(R^3_z)]_y$, wherein x=1-2, y=1-2, z=0-1, x+z=1-3, and each $R^1$ and $R^3$ independently has the formula $H_aF_bC_c$ with a=1-11, b=0-11, and c=0-5;

the organofluorine compound being hexafluoroacetone imine ($C_3HF_6N$) having the formula

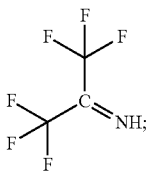

the organofluorine compound being 1,1,1,6,6,6-Hexafluoro-3-azahex-3-ene ($C_5H_5F_6N$) having the formula

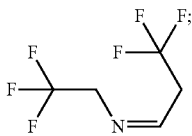

the activated nitrogen containing etching compound reacting with the silicon-containing film to form volatile by-products;

the volatile by-products being removed from the reaction chamber;

the inert gas being selected from the group consisting of He, Ar, Xe, Kr, and Ne;

the inert gas being Ar;

mixing the vapor of the nitrogen containing etching compound and the inert gas prior to introduction to the reaction chamber to produce a mixture;

introducing the vapor of the nitrogen containing etching compound into the reaction chamber separately from the inert gas;

introducing the inert gas continuously into the reaction chamber and introducing the vapor of the nitrogen containing etching compound into the reaction chamber in pulses;

the inert gas comprising approximately 0.01% v/v to approximately 99.9% v/v of a total volume of the vapor of the nitrogen containing etching compound and inert gas introduced into the reaction chamber;

the inert gas comprising approximately 90% v/v to approximately 99% v/v of a total volume of the vapor of the nitrogen containing etching compound and inert gas introduced into the reaction chamber;

introducing an oxidizer into the reaction chamber;

not introducing an oxidizer into the reaction chamber;

the oxidizer being selected from the group consisting of $O_2$, CO, $CO_2$, NO, $N_2O$, and $NO_2$;

the oxidizer being $O_2$;

mixing the vapor of the nitrogen containing etching compound and the oxidizer prior to introduction into the reaction chamber;

introducing the vapor of the nitrogen containing etching compound into the reaction chamber separately from the oxidizer;

introducing the oxidizer continuously into the reaction chamber and introducing the vapor of the nitrogen containing etching compound into the reaction chamber in pulses;

the oxidizer comprising approximately 0.01% v/v to approximately 99.9% v/v of a total volume of the vapor of the nitrogen containing etching compound and oxidizer introduced into the reaction chamber;

the oxidizer comprising approximately 0.01% v/v to approximately 10% v/v of a total volume of the vapor of the nitrogen containing etching compound and oxidizer introduced into the reaction chamber;

the silicon-containing film comprising a layer of silicon oxide, silicon nitride, polysilicon, crystalline silicon, SiON, SiOCH, $Si_aO_bC_cN_dH_e$ (where a>0; b, c, d and e≥0) or combinations thereof;

the silicon-containing film comprising oxygen atoms, nitrogen atoms, carbon atoms, hydrogen atoms or combinations thereof;

the silicon-containing film comprising silicon carbide;

the silicon-containing film being selectively etched from an a-C layer;

the silicon-containing film being selectively etched from a photoresist layer;

the silicon-containing film being selectively etched from a silicon nitride layer;

the silicon-containing film being selectively etched from a polysilicon layer;

the silicon-containing film being selectively etched from a crystalline silicon layer;

the silicon-containing film being selectively etched from a metal contact layer;

the silicon-containing film being selectively etched from a Titanium Nitride layer;

the silicon-containing film being selectively etched from a Tantalum layer;

the silicon-containing film being a silicon oxide layer;

selectively etching the silicon oxide layer from an a-C layer;

selectively etching the silicon oxide layer from a photoresist layer;

selectively etching the silicon oxide layer from a p-Si layer;

selectively etching the silicon oxide layer from a crystalline silicon layer;

selectively etching the silicon oxide layer from a metal contact layer;

selectively etching the silicon oxide layer from a SiN layer;

the silicon-containing film being a silicon nitride layer;

selectively etching the silicon nitride layer from an a-C layer;

selectively etching the silicon nitride layer from a patterned photoresist layer;

selectively etching the silicon nitride layer from a p-Si layer;

selectively etching the silicon nitride layer from a crystalline silicon layer;

selectively etching the silicon nitride layer from a metal contact layer;

selectively etching the silicon nitride layer from a silicon oxide layer;
the silicon-containing film being a SiON layer;
selectively etching the SiON layer from photoresist layer;
the silicon-containing film being a SiCOH layer;
selectively etching the SiCOH layer from titanium nitride layer;
selectively etching the SiCOH layer from a-C layer;
selective etching the SiCOH layer from photoresist layer;
the silicon-containing film being alternating silicon oxide and silicon nitride layers;
etching both silicon oxide and silicon nitride layers at similar etch rates;
selectively etching both silicon oxide and silicon nitride layers from a silicon layer;
selectively etching both silicon oxide and silicon nitride layers from a p-Si layer;
selectively etching both silicon oxide and silicon nitride layers from a crystalline silicon layer;
selectively etching both silicon oxide and silicon nitride layers from an a-C layer;
the silicon-containing film being alternating silicon oxide and p-Si layers;
etching both silicon oxide and p-Si layers at similar etch rates;
selectively etching both silicon oxide and p-Si layers from an a-C layer;
selectively etching both silicon oxide and p-Si layers from a silicon nitride layer;
producing an aperture in the silicon-containing film having an aspect ratio between approximately 10:1 and approximately 200:1;
producing a gate trench;
producing a staircase contact;
producing a channel hole;
producing a channel hole having an aspect ratio between approximately 60:1 and approximately 100:1;
producing a channel hole having a diameter ranging from approximately 5 nm to approximately 100 nm;
producing a channel hole having a diameter ranging from approximately 10 nm to approximately 50 nm;
improving selectivity by introducing an etch gas into the reaction chamber;
the etch gas being selected from the group consisting of $cC_4F_8$, $C_4F_8$, $C_4F_6$, $CF_4$, $CH_3F$, $CF_3H$, $CH_2F_2$, COS, $CF_3I$, $C_2F_3I$, $C_2F_5I$, F—C≡N, $CS_2$, $SO_2$, trans-1,1,1,4,4,4-hexafluoro-2-butene (trans-$C_4H_2F_6$), cis-1,1,1,4,4,4-hexafluoro-2-butene (cis-$C_4H_2F_6$), hexafluoroisobutene ($C_4H_2F_6$), trans-1,1,2,2,3,4-hexafluorocyclobutane (trans-$C_4H_2F_6$), 1,1,2,2,3-pentafluorocyclobutane ($C_4H_3F_5$), 1,1,2,2-tetrafluorocyclobutane ($C_4H_4F_4$), or cis-1,1,2,2,3,4-hexafluorocyclobutane (cis-$C_4H_2F_6$);
the etch gas being $cC_5F_8$;
the etch gas being $cC_4F_8$;
the etch gas being $C_4F_6$;
mixing the vapor of the nitrogen containing etching compound and the etch gas prior to introduction to the reaction chamber;
introducing the vapor of the nitrogen containing etching compound into the reaction chamber separately from the etch gas;
introducing approximately 0.01% v/v to approximately 99.99% v/v of the etch gas into the reaction chamber;
activating the plasma by applying RF power;
activating the plasma by a RF power ranging from approximately 25 W to approximately 10,000 W;
the reaction chamber having a pressure ranging from approximately 1 mTorr to approximately 10 Torr;
introducing the vapor of the nitrogen containing etching compound into the reaction chamber at a flow rate ranging from approximately 0.1 sccm to approximately 1 slm;
maintaining the substrate at a temperature ranging from approximately −196° C. to approximately 500° C.;
maintaining the substrate at a temperature ranging from approximately −120° C. to approximately 300° C.;
maintaining the substrate at a temperature ranging from approximately −100° C. to approximately 50° C.;
maintaining the substrate at a temperature ranging from approximately −10° C. to approximately 40° C.; and
measuring the activated nitrogen containing etching compound by Quadrupole mass spectrometer, optical emission spectrometer, FTIR, or other radical/ion measurement tool.

Also disclosed are nitrogen containing etching compound comprising an organofluorine compound having a C≡N or C═N functional group. The disclosed nitrogen containing etching compounds include one or more of the following aspects:

the organofluorine compound containing a C≡N functional group;
the organofluorine compound having the formula N≡C—$R^1$, wherein $R^1$ has the formula $H_aF_bC_c$ and a=0, b=1-11, and c=1-5;
the organofluorine compound being trifluoroacetonitrile ($C_2F_3N$) having the formula

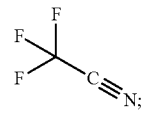

the organofluorine compound being nonafluoropentanitrile ($C_5F_9N$) having the formula

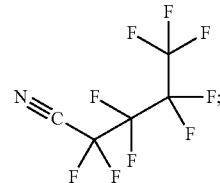 [SMILES: N#CC(F)(F)C(F)(F)C(F)(F)C(F)(F)F]

the organofluorine compound being pentafluoroallyl cyanide ($C_4F_5N$) having the formula

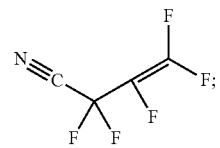

the organofluorine compound having the formula N≡C—$R^1$, wherein $R^1$ has the formula $H_aF_bC_c$ and a=1-11, b=1-11, and c=1-5;
the organofluorine compound being difluoroacetonitrile ($C_2HF_2N$) having the formula

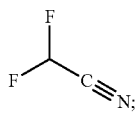

the organofluorine compound being 2,3,3,3-tetrafluoro-propionitrile ($C_3HF_4N$) having the formula

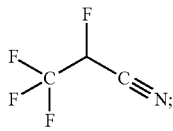

the organofluorine compound being 2,2,3,3-tetrafluoro-propionitrile ($C_3HF_4N$) having the formula

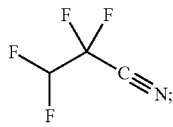

the organofluorine compound being 4,4,4-Trifluorocrotono-nitrile ($C_4H_2F_3N$) having the formula

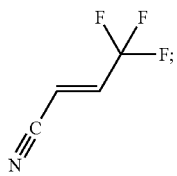

the organofluorine compound being 3,3,3-Trifluoropropionitrile ($C_4H_2F_3N$) having the formula

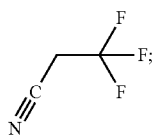

the organofluorine compound being fluoroacetonitrile ($C_2H_2FN$) having the formula

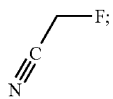

the organofluorine compound having the formula (N≡C—)—($R^1$)—(—C≡N), wherein each $R^1$ independently has the formula $H_aF_bC_c$ with a=0, b=1-11, and c=1-5;

the organofluorine compound being octafluorohexane-1,6-dinitrile ($C_6F_8N_2$) having the formula

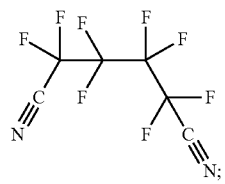 [SMILES: N#CC(F)(F)C(F)(F)C(F)(F)C(F)(F)C#N]

the organofluorine compound being 1,1-bis(trifluoromethyl)-2,2-dicyanoethylene ($C_6F_6N_2$) having the formula

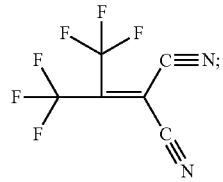 [SMILES: N#CC(C#N)=C(C(F)(F)F)C(F)(F)F]

the organofluorine compound having the formula (N≡C—)—($R^1$)—(—C≡N), wherein each $R^1$ independently has the formula $H_aF_bC_c$ with a=1-11, b=1-11, and c=1-5;

the organofluorine compound being 2-[1-(difluoromethyl)-2,2,2-trifluoroethylidene]-propanedinitrile ($C_6HF_5N_2$) having the formula

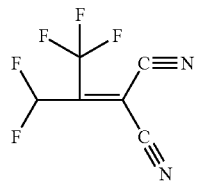 [SMILES: N#CC(C#N)=C(C(F)F)C(F)(F)F]

the organofluorine compound containing a C≡N functional group;

the organofluorine compound having the formula $R^1_x[—C=N(R^2_z)]_y$, wherein x=1-2, y=1-2, z=0-1, x+z=1-3, and each $R^1$ and $R^2$ independently has the formula $H_aF_bC_c$ with a=0, b=0-11, and c=0-5;

the organofluorine compound being N,1,1,1,3,3,3-heptafluoro-propanamine ($C_3F_7N$) having the formula

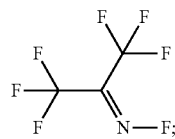

the organofluorine compound having the formula $R^1_x[—C=N(R^2_z)]_y$, wherein x=1-2, y=1-2, z=0-1, x+z=1-3, and each $R^1$ and $R^2$ independently has the formula $H_aF_bC_c$ with a=1-11, b=0-11, and c=0-5;

the organofluorine compound being hexafluoroacetone imine ($C_3HF_6N$) having the formula

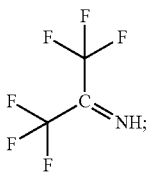

the organofluorine compound being 1,1,1,6,6,6-Hexafluoro-3-azahex-3-ene ($C_5H_5F_6N$) having the formula

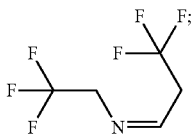

having a purity ranging from approximately 95% to approximately 99.999% by volume;
comprising between approximately 10 parts per trillion to approximately 5% by volume trace gas impurities;
the trace gas impurities comprising water;
the trace gas impurities comprising $CO_2$;
the trace gas impurities comprising $N_2$; and
the nitrogen containing etching compound having a water content of less than 20 ppmw.

NOTATION AND NOMENCLATURE

The following detailed description and claims utilize a number of abbreviations, symbols, and terms, which are generally well known in the art. While definitions are typically provided with the first instance of each acronym, for convenience, Table 1 provides a list of the abbreviations, symbols, and terms used along with their respective definitions.

TABLE 1

| | |
|---|---|
| a or an | one or more than one |
| approximately or about | ±10% of the value stated |
| LCD-TFT | liquid-crystal display-thin-film transistor |
| DRAM | dynamic random-access memory |
| FINFET | fin-shaped field-effect transistor |
| Bulk CMOS | Bulk complementary metal-oxide-semiconductor |
| FD-SOI | fully depleted silicon-on-insulator |
| FEOL | front end of the line |
| BEOL | back end of the line |
| TSV | through silicon via |
| OLED | organic light-emitting diode |
| RIE | reactive ion etching |
| CCP | capacitively coupled plasma |
| ICP | inductively coupled plasma |
| sccm | standard cubic centimeters per minute |
| slm | standard liter per minute |
| ONON | silicon oxide and silicon nitride alternating layers |
| TCAT | terabit cell array transistor |
| P-BICS | pipe-shaped bit cost scalable |
| QMS | Quadrupole mass spectrometer |
| ARC or BARC | Anti-reflecting coating or Bottom anti-reflecting coating |
| APF or a-C | Amorphous carbon. Trademark of Applied Materials |
| CAS | chemical abstract service |
| PCTFE | Polychlorotrifluoroethene |
| PVDF | polyvinylidene fluoride |
| PTFE | Polytetrafluoroethylene |
| SEM | scanning electron microscope |

TABLE 1-continued

| | |
|---|---|
| NAND | Not AND or Negative-NAND or Negated AND |
| TEOS | Tetraethylorthosilicate |
| LDTEOS | low deposition rate TEOS |
| BPSG | Borophosphosilicateglass |
| p-Si | poly-silicon |
| XPS | X-ray photoelectron spectroscopy |
| SiN | Silicon nitride |
| SiO | Silicon oxide |

As used herein, the term "etch" or "etching" refers to a plasma etch process (i.e., a dry etch process) in which ion bombardment accelerates the chemical reaction in the vertical direction so that vertical sidewalls are formed along the edges of the masked features at right angles to the substrate (Manos and Flamm, Plasma Etching An Introduction, Academic Press, Inc. 1989 pp. 12-13). The etching process produces apertures, such as vias, trenches, channel holes, gate trenches, staircase contacts, capacitor holes, contact holes, etc., in the substrate.

The term "pattern etch" or "patterned etch" refers to etching a non-planar structure, such as a patterned mask layer on a stack of silicon-containing films.

The term "mask" refers to a layer that resists etching. The mask layer may be located above the layer to be etched.

The term "etch stop" refers to a layer below the layer to be etched that protects layers underneath.

The term "device channel" refers to layers that are part of actual device and any damage to it will affect device performance.

The term "aspect ratio" refers to a ratio of the height of a trench (or via) to the width of the trench (or the diameter of the via).

The term "selectivity" means the ratio of the etch rate of one material to the etch rate of another material. The term "selective etch" or "selectively etch" means to etch one material more than another material, or in other words to have a greater or less than 1:1 etch selectivity between two materials.

The term "independently" when used in the context of describing R groups should be understood to denote that the subject R group is not only independently selected relative to other R groups bearing the same or different subscripts or superscripts, but is also independently selected relative to any additional species of that same R group. For example in the formula $MR^1_x(NR^2R^3)_{(4-x)}$, where M is an atom, x is 2 or 3, the two or three $R^1$ groups may, but need not be identical to each other or to $R^2$ or to $R^3$. Further, it should be understood that unless specifically stated otherwise, values of R groups are independent of each other when used in different formulas.

Note that herein, the terms "film" and "layer" may be used interchangeably. It is understood that a film may correspond to, or related to a layer, and that the layer may refer to the film. Furthermore, one of ordinary skill in the art will recognize that the terms "film" or "layer" used herein refer to a thickness of some material laid on or spread over a surface and that the surface may range from as large as the entire wafer to as small as a trench or a line.

Note that herein, the terms "etching compound" and "etching gas" may be used interchangeably. It is understood that an etching compound may correspond to, or related to an etching gas, and that the etching gas may refer to the etching compound.

As used herein, the abbreviation "NAND" refers to a "Negated AND" or "Not AND" gate; the abbreviation "2D" refers to 2 dimensional gate structures on a planar substrate;

the abbreviation "3D" refers to 3 dimensional or vertical gate structures, wherein the gate structures are stacked in the vertical direction.

The standard abbreviations of the elements from the periodic table of elements are used herein. It should be understood that elements may be referred to by these abbreviations (e.g., Si refers to silicon, N refers to nitrogen, O refers to oxygen, C refers to carbon, H refers to hydrogen, F refers to fluorine, etc.).

The unique CAS registry numbers (i.e., "CAS") assigned by the Chemical Abstract Service are provided to help better identify the molecules disclosed.

Please note that the silicon-containing films, such as SiN and SiO, are listed throughout the specification and claims without reference to their proper stoichoimetry. The silicon-containing films may include pure silicon (Si) layers, such as crystalline Si, poly-silicon (p-Si or polycrystalline Si), or amorphous silicon; silicon nitride ($Si_kN_l$) layers; or silicon oxide ($Si_nO_m$) layers; or mixtures thereof, wherein k, l, m, and n, inclusively range from 0.1 to 6. Preferably, silicon nitride is $Si_kN_l$, where k and l each range from 0.5 to 1.5. More preferably silicon nitride is $Si_3N_4$. Preferably silicon oxide is $Si_nO_m$, where n ranges from 0.5 to 1.5 and m ranges from 1.5 to 3.5. More preferably, silicon oxide is $SiO_2$. Herein, SiO in the following description may be used to represent $Si_nO_m$ containing layers. The silicon-containing film could also be a silicon oxide based dielectric material such as organic based or silicon oxide based low-k dielectric materials such as the Black Diamond II or III material by Applied Materials, Inc. with a formula of SiOCH. Silicon-containing film may also include $Si_aO_bN_c$ where a, b, c range from 0.1 to 6. The silicon-containing films may also include dopants, such as B, C, P, As and/or Ge.

BRIEF DESCRIPTION OF THE DRAWINGS

For a further understanding of the nature and objects of the present invention, reference should be made to the following detailed description, taken in conjunction with the accompanying drawings, in which like elements are given the same or analogous reference numbers and wherein:

FIG. 1b is an exemplary cross-sectional side view of the exemplary layers in the 3D NAND stack showing polymer deposited on a sidewall during etching in the 3D NAND stack;

FIG. 1d is an exemplary cross-sectional side view of the exemplary layers in the 3D NAND stack showing selective etching of SiN exposed on the sidewall in the 3D NAND stack after etching;

FIG. 3a is an exemplary cross-sectional side view of exemplary layers showing photoresist pattern over SiO insulation layer surrounding typical transistor device region to produce a transistor structure;

DESCRIPTION OF PREFERRED EMBODIMENTS

Figure 1A:
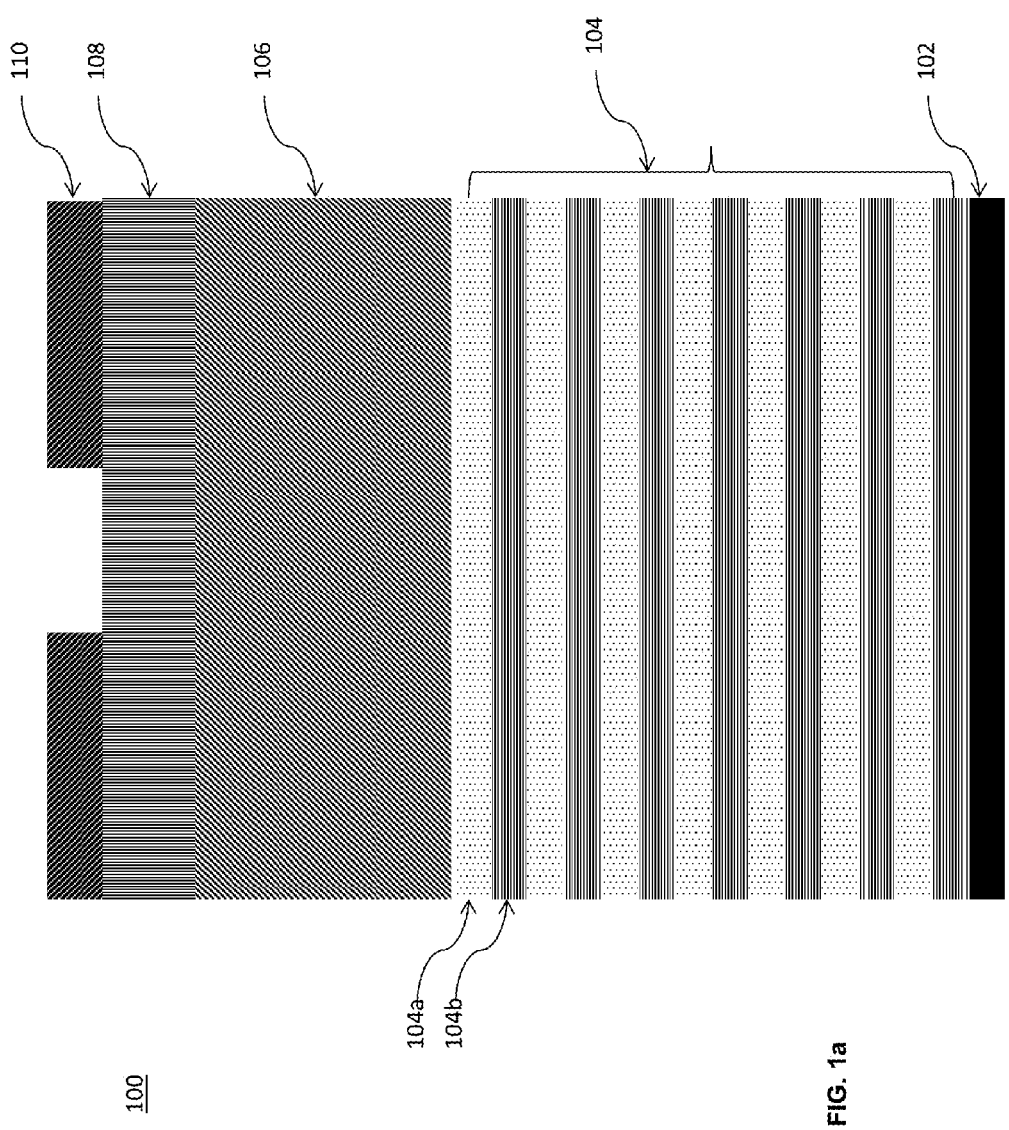
FIG. 1a is an exemplary cross-sectional side view of exemplary layers in a 3D NAND stack to produce a 3D NAND gate in the art.

Disclosed are methods for plasma etching semiconductor structures, such as, channel holes, gate trenches, staircase contacts, capacitor holes, contact holes, etc., in silicon-containing films. The disclosed methods include the steps of i) introducing a vapor of a nitrogen containing etching compound into a reaction chamber containing a silicon-containing film on a substrate, wherein the nitrogen containing etching compound is an organofluorine compound containing at least one C≡N or C═N functional group; ii) introducing an inert gas into the reaction chamber; and iii) activating a plasma to produce an activated nitrogen containing etching compound capable of etching the silicon-containing film from the substrate. Herein the organofluorine compounds are organic compounds that contain a carbon-fluorine (C—F) bonds The disclosed organofluorine compounds comprising at least one C≡N functional group have the general formulae:

$$N≡C—R^1 \quad (I)$$

$$(N≡C—)(R^1)(—C≡N) \quad (II)$$

wherein $R^1$-$R^3$ may each independently be a functional group having the formula $H_aF_bC_c$ with a=0-11, b=1-11, and c=0-5. The $H_aF_bC_c$ functional group may be linear, branched, or cyclic and saturated or unsaturated. Applicants believe that the C≡N functionality may provide improved etch resistant polymer deposition benefits compared to $C_xF_y$ polymers, wherein x ranges from 0.01 to 1 and y ranges from 0.01 to 4. When the organofluorine compound includes at least one H, the etch rate of SiN may be enhanced while maintaining high selectivity to the mask layer.

The disclosed organofluorine compounds comprising at least one C═N functional group have the general formula:

$$R^1{}_x[—C═N(R^2{}_z)]_y \quad (III)$$

wherein x=1-2, y=1-2, z=0-1, x+z=1-3, and each $R^1$ and $R^2$ independently has the formula $H_aF_bC_c$ with a=0-11, b=0-11, and c=0-5. The $H_aF_bC_c$ functional group may be linear, branched, or cyclic and saturated or unsaturated. Applicants believe that the C═N functionality may provide improved selectivity among silicon layers compared to $C_xF_y$ polymers, wherein x ranges from 0.01 to 1 and y ranges from 0.01 to 4. When the organofluorine compound includes at least one H, and preferably when $R^2$ is H, the etch rate of SiN may be enhanced while maintaining high selectivity to the mask layer.

The disclosed organofluorine compounds may be a hydrofluorocarbon ($C_xH_yF_z$) or fluorocarbon ($C_mF_n$) compound containing at least one C≡N or C═N functional group, or a hetero-hydrofluorocarbon ($C_xH_yF_z$) or hetero-fluorocarbon ($C_mF_n$) compound containing at least one C≡N or C═N functional group, where m, n, x, y and z are integers.

The disclosed nitrogen containing etching compounds include: difluoroacetonitrile ($C_2HF_2N$), trifluoroacetonitrile ($C_2F_3N$), 2,3,3,3-tetrafluoropropionitrile ($C_3HF_4N$), 2,2,3,3-tetrafluoropropionitrile ($C_3HF_4N$), Nonafluoropentanitrile ($C_5F_9N$), Pentafluoroallyl cyanide ($C_4F_5N$); or Hexafluoroacetone imine ($C_3HF_6N$), which are listed in Table 2. These molecules are commercially available and their structure formula, CAS numbers and boiling points are also included in Table 2.

TABLE 2

Commercially available etching compounds

| Etching compounds | Formula | Structure | CAS number | Boiling point (° C.) |
|---|---|---|---|---|
| difluoroacetonitrile | $C_2HF_2N$ | 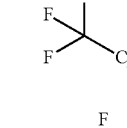 | 359-12-6 | 23 |
| trifluoroacetonitrile | $C_2F_3N$ | 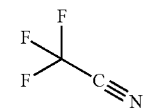 | 353-85-5 | −64 |
| 2,3,3,3-tetrafluoropropionitrile | $C_3HF_4N$ | 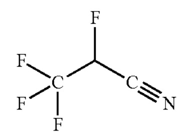 | 431-32-3 | 40 |
| 2,2,3,3-tetrafluoropropionitrile | $C_3HF_4N$ | 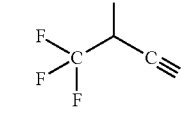 | 425-85-4 | 27 |
| Nonafluoropentanitrile | $C_5F_9N$ | 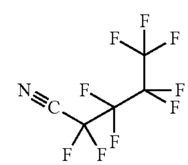 [SMILES: N#CC(F)(F)C(F)(F)C(F)(F)C(F)(F)F] | 22325-71-9 | 15 |
| Pentafluoroallyl cyanide | $C_4F_5N$ | 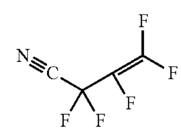 | 7792-66-7 | 46-48 |
| Hexafluoroacetone imine | $C_3HF_6N$ | 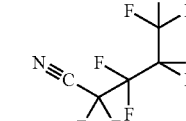 | 1645-75-6 | 16.5 |
| 4,4,4-Trifluorocrotononitrile | $C_4H_2F_3N$ | 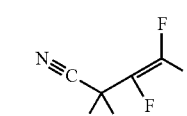 | 406-86-0 | 84-85 |
| 3,3,3-Trifluoropropionitrile | $C_3H_2F_3N$ | 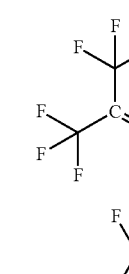 | 20530-38-5 | 92 |
| fluoroacetonitrile | $C_2H_2FN$ | 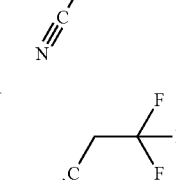 | 503-20-8 | 79-80 |
| octafluorohexane-1,6-dinitrile | $C_6F_8N_2$ | 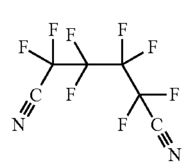 [SMILES: N#CC(F)(F)C(F)(F)C(F)(F)C(F)(F)C#N] | 376-53-4 | 63-64 |

TABLE 2-continued

Commercially available etching compounds

| Etching compounds | Formula | Structure | CAS number | Boiling point (° C.) |
|---|---|---|---|---|
| 1,1-bis(trifluoromethyl)-2,2-dicyanoethylene | $C_6F_6N_2$ | | 1113-69-5 | 226.2 |
| 1-trifluoromethyl,1-difluoromethyl,-2,2-dicyanoethylene | $C_6HF_5N_2$ | 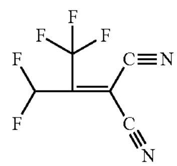 [SMILES: N#CC(C#N)=C(C(F)F)C(F)(F)F] | 439913-54-9 | 255.9 |
| N,1,1,1,3,3,3-heptafluoro-propanamine | $C_3F_7N$ | 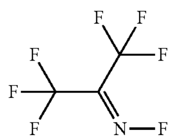 [SMILES: FN=C(C(F)(F)F)C(F)(F)F] | 2802-70-2 | −25 |
| 1,1,1,6,6,6-Hexafluoro-3-azahex-3-ene | $C_5H_5F_6N$ | 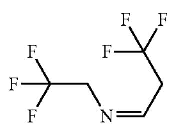 [SMILES: FC(F)(F)C/C=N\CC(F)(F)F] | 885275-84-3 | 87 |

The disclosed nitrogen containing etching compounds may also include 4,4,4-Trifluorocrotononitrile ($C_4H_2F_3N$); 3,3,3-Trifluoropropionitrile ($C_3H_2F_3N$); fluoroacetonitrile ($C_2H_2FN$); octafluorohexane-1,6-dinitrile ($C_6F_8N_2$); 1,1-bis(trifluoromethyl)-2,2-dicyanoethylene ($C_6F_6N_2$); N,1,1,1,3,3,3-heptafluoro-propanamine ($C_3F_7N$); 1,1,1,6,6,6-Hexafluoro-3-azahex-3-ene ($C_5H_5F_6N$). Their structure formula, CAS numbers and boiling points or predicted boiling points are also included in Table 2. One of ordinary skill in the art will recognize that the synthesis methods for these compounds may be obtained using the CAS numbers provided.

The disclosed nitrogen-containing etching compounds may provide high selectivity to mask layers, etch stop layers and device channel materials and no profile distortion in high aspect ratio structures, such as those having an aspect ratio ranging from 10:1 to 200:1 such as DRAM and 3D NAND applications. Alternatively, the disclosed nitrogen-containing etching compounds may also provide high selectivity to mask layers or silicon nitride, such as those having an aspect ratio ranging from 1:1 to 50:1 in contact etch applications.

The disclosed nitrogen-containing etching compounds may provide infinite selectivity for wide process conditions of etching. Herein the selectivity refers to the etching rate ratio of two different layers. For example, the selectivity for SiO layer vs. a-C layer is the etch rate of the SiO divided by the etching rate of the a-C layer. The disclosed nitrogen-containing etching compounds may provide improved selectivity between the silicon-containing films and mask materials, less damage to channel region, and reduced bowing in pattern high aspect ratio structures. The disclosed nitrogen-containing etching compounds may also etch through alternating layers of p-Si, SiO, and/or SiN, resulting in a vertical etch profile (i.e., demonstrating selectivity ranging from 2:1 to 1:2 between the alternating layers).

The disclosed nitrogen-containing etching compounds are provided at greater than 95% v/v purity, preferably at greater than 99.99% v/v purity, and more preferably at greater than 99.999% v/v purity. The disclosed nitrogen-containing etching compounds contain less than 5% by volume trace gas impurities, with less than 150 ppm by volume of impurity gases, such as $N_2$ and/or $H_2O$ and/or $CO_2$, contained in said trace gaseous impurities. Preferably, the water content in the plasma etching gas is less than 20 ppmw by weight. The purified product may be produced by distillation and/or passing the gas or liquid through a suitable adsorbent, such as a 4 A molecular sieve.

The disclosed nitrogen-containing etching compounds contain less than 10% v/v, preferably less than 1% v/v, more preferably less than 0.1% v/v, and even more preferably less than 0.01% v/v of any of its isomers, which may be purified by distillation of the gas or liquid to remove isomers and may provide better process repeatability.

Alternatively, the disclosed nitrogen-containing etching compounds may contain between 5% v/v and 50% v/v of its isomers, particularly when the isomer mixture provides improved process parameters or if isolation of the target isomer is too difficult or expensive. For example, the disclosed nitrogen-containing etching compounds may comprise between approximately 50% v/v and approximately 75% v/v 2,3,3,3-tetrafluoropropionitrile and between approximately 25% v/v and approximately 50% v/v 2,2,3,3-tetrafluoropropionitrile. The mixture of isomers may reduce the need for two or more gas lines to the reaction chamber.

Some of the disclosed nitrogen-containing etching compounds are gaseous at room temperature and atmospheric pressure. For the non-gaseous (i.e., liquid or solid) compounds, their gas form may be produced by vaporizing the compounds through a conventional vaporization step, such as direct vaporization or by bubbling. The non-gaseous compounds may be fed in liquid state to a vaporizer where it is vaporized before it is introduced into a reactor.

The disclosed nitrogen-containing etching compounds are suitable for plasma etching semiconductor structures, such as, channel holes, gate trenches, staircase contacts, capacitor holes, contact holes, etc., in the silicon-containing films. The disclosed nitrogen-containing etching compounds are not only compatible with currently available mask materials but also compatible with the future generations of mask materials because the disclosed nitrogen-containing etching compounds induce little to no damage on the mask along with good profile of high aspect ratio structures. In order to achieve these properties, the disclosed nitrogen-containing etching compounds may deposit an etch-resistant polymer layer during etching to help reduce the direct impact of the oxygen and fluorine radicals during the etching process. The disclosed nitrogen-containing etching compounds may also reduce damage to p-Si or crystalline Si channel structure during etching. Preferably, the disclosed nitrogen-containing etching compounds are suitably volatile and stable during the etching process for delivery into the reactor/chamber.

Material compatibility tests are important to determine if any of the disclosed nitrogen-containing etching compounds will react with chamber materials and degrade the performance of the chamber with short term or long term use. Key materials involved in parts of the chamber, valves, etc. include stainless steel, aluminum, nickel, PCTFE, PVDF, PTFE and other metals and polymers. At times these materials are exposed to high temperatures, for example, higher than 20° C., and high pressures, for example, higher than 1 atm, which may enhance their degradation. The metrology methods may include visual inspection, weight measurement, measuring nanometer scale changes in SEM, tensile strength, hardness, etc.

The disclosed nitrogen-containing etching compounds may be used to plasma etch silicon-containing films on a substrate. The disclosed plasma etching method may be useful in the manufacture of semiconductor devices such as NAND or 3D NAND gates or Flash or DRAM memory or transistors such as fin-shaped field-effect transistor (FinFET), Bulk complementary metal-oxide-semiconductor (Bulk CMOS), fully depleted silicon-on-insulator (FD-SOI) structures. The disclosed nitrogen-containing etching compounds may be used in other areas of applications, such as different front end of the line (FEOL) and back end of the line (BEOL) etch applications. Additionally, the disclosed nitrogen-containing etching compounds may also be used for etching Si in 3D through silicon via (TSV) etch applications for interconnecting memory to logic on a substrate.

The plasma etching method includes providing a reaction chamber having a substrate disposed therein. The reaction chamber may be any enclosure or chamber within a device in which etching methods take place such as, and without limitation, reactive ion etching (RIE), capacitively coupled plasma (CCP) with single or multiple frequency RF sources, inductively coupled plasma (ICP), or microwave plasma reactors, or other types of etching systems capable of selectively removing a portion of the silicon-containing film or generating active species. One of ordinary skill in the art will recognize that the different plasma reaction chamber designs provide different electron temperature control. Suitable commercially available plasma reaction chambers include but are not limited to the Applied Materials magnetically enhanced reactive ion etcher sold under the trademark eMAX™ or the Lam Research Dual CCP reactive ion etcher dielectric etch product family sold under the trademark 2300® Flex™. The RF power in such may be pulsed to control plasma properties and thereby improving the etch performance (selectivity and damage) further.

Alternatively, the plasma-treated reactant may be produced outside of the reaction chamber. The MKS Instruments' ASTRONi® reactive gas generator may be used to treat the reactant prior to passage into the reaction chamber. Operated at 2.45 GHz, 7 kW plasma power, and a pressure ranging from approximately 0.5 Torr to approximately 10 Torr, the reactant $O_2$ may be decomposed into two O. radicals. Preferably, the remote plasma may be generated with a power ranging from about 1 kW to about 10 kW, more preferably from about 2.5 kW to about 7.5 kW.

The reaction chamber may contain one or more than one substrate. For example, the reaction chamber may contain from 1 to 200 silicon wafers having from 25.4 mm to 450 mm diameters. The substrates may be any suitable substrates used in semiconductor, photovoltaic, flat panel or LCD-TFT device manufacturing. Examples of suitable substrates include wafers, such as silicon, silica, glass, or GaAs wafers. The wafer will have multiple films or layers on it from previous manufacturing steps, including silicon-containing films or layers. The layers may or may not be patterned. Examples of suitable layers include without limitation silicon (such as amorphous silicon, p-Si, crystalline silicon, any of which may further be p-doped or n-doped with B, C, P, As, and/or Ge), silica, silicon nitride, silicon oxide, silicon oxynitride, $Si_aO_bH_cC_dN_e$, (where a>0; b, c, d, e≥0), mask layer materials such as amorphous carbon, antireflective coatings, photoresist materials, tungsten, titanium nitride, tantalum nitride or combinations thereof, etch stop layer materials such as silicon nitride, polysilicon, crystalline silicon, silicon carbide, SiCN or combinations thereof, device channel materials such crystalline silicon, epitaxial silicon, doped silicon, $Si_aO_bH_cC_dN_e$, (where a>0; b, c, d, e≥0) or combinations thereof. The silicon oxide layer may form a dielectric material, such as an organic based or silicon oxide based low-k dielectric material (e.g., a porous SiCOH film). An exemplary low-k dielectric material is sold by Applied Materials under the trade name Black Diamond II or III. Additionally, layers comprising tungsten or noble metals (e.g. platinum, palladium, rhodium or gold) may be used. Furthermore, examples of the silicon-containing films may be $Si_aO_bH_cC_dN_e$, (where a>0; b, c, d, e≥0). Throughout the specification and claims, the wafer and any associated layers thereon are referred to as substrates.

The following are exemplary embodiments of the substrates on which the disclosed nitrogen-containing etching compounds may be applied to etch.

In one embodiment, a substrate 100 may include a stack of multiple layers as shown in FIG. 1a. FIG. 1a is a cross-sectional side view of exemplary layers in a 3D NAND stack to produce a 3D NAND gate. In FIG. 1a, a stack of seven alternative SiO/SiN (i.e., 104a/104b) layers 104 is located on top of a silicon wafer 102 (i.e., ONON or TCAT technology). One of ordinary skill in the art will recognize that some technologies replace the SiN layers 104a with p-Si layers (e.g., SiO/p-Si or P—BICS technology). An a-C mask layer 106 is located on the top of the seven SiO/SiN layers 104. The a-C mask layer 106 may contain C and H, as well as other elements, such as boron, nitrogen, etc., to improve etch resistance during SiO/SiN layer etch. An antireflective coating layer 108 is located on top of the a-C mask layer 106. A patterned photoresist layer 110 is located on top of the antireflective coating layer 108. Herein, a SiON layer (not shown) may be present between the antireflective coating layer 108 and the a-C mask layer 106 to transfer pattern in photoresist layer 110 to the a-C layer 106. One of ordinary skill in the art will recognize that the stack of layers in the substrate 100 in FIG. 1a is provided for exemplary purposes only and that the disclosed nitrogen-containing etching compounds may be used to etch other types of stacks of layers. Furthermore, one of ordinary skill in the art will recognize that the number alternating SiO/SiN or SiO/p-Si layers 104 in the stack of the substrate 100 may vary (i.e., may include more or less than the seven SiO/SiN (104a/104b) layers depicted).

FIG. 1b is a cross-sectional side view of the exemplary layers in the 3D NAND stack showing polymer deposited on a sidewall during etching. The disclosed nitrogen containing compounds may produce fragments during the plasma process that are suitable for both anisotropically etching the silicon-containing films 104 and depositing a N-containing polymer passivation layer 212 on sidewalls of a structure being etched as shown in FIG. 1b. The difference between FIG. 1b and FIG. 1a is in FIG. 1b via 214 is formed in substrate 200 by plasma etching using the disclosed nitrogen-containing etch compounds, which also deposit the polymer passivation layer 212 on the sidewalls of the via 214. The polymer passivation layer 212 also provides smoother sidewall, less bowing and less deformation at the bottom of the via 214. The polymer passivation layer 212 may however be easily removed or cleaned by dry or wet etch chemistries well known in the art.

Figure 1C:
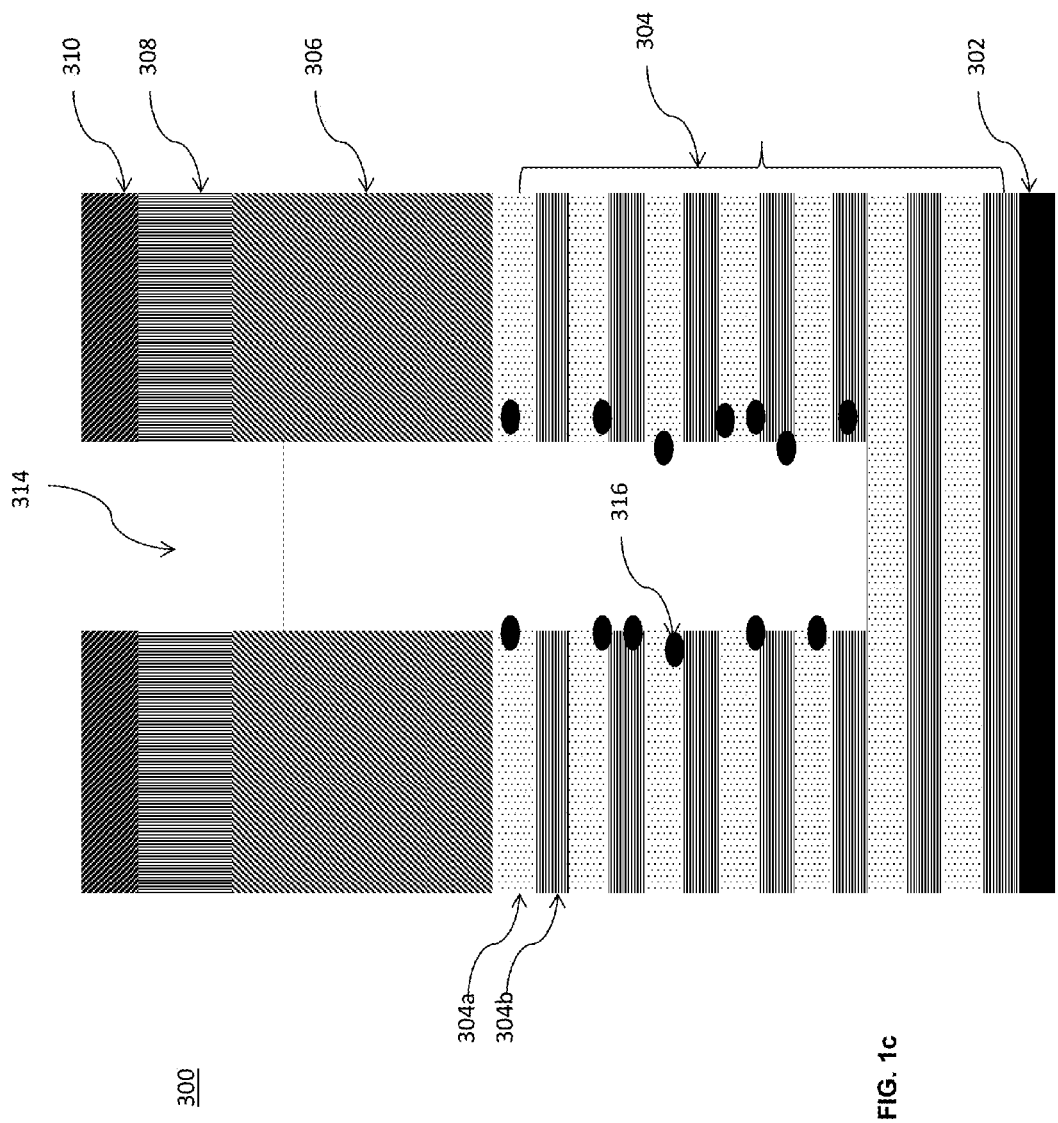
FIG. 1c is an exemplary cross-sectional side view of the exemplary layers in the 3D NAND stack showing particles generation during alternating SiO/SiN layer etching in a 3D NAND stack.

FIG. 1c is a cross-sectional side view of the exemplary layers in the 3D NAND stack showing particles 316 generated during alternating SiO/SiN layer etching in a 3D NAND stack. The particles 316 generated on the sidewalls of the alternative SiO/SiN (i.e., 304a/304b) layers 304 as shown in FIG. 1c may be minimized by using the disclosed nitrogen-containing compounds. The difference between FIG. 1c and FIG. 1b is in FIG. 1c the alternative SiO/SiN exposed sidewall has particle 316 generated during plasma etching. Applicants do not believe that the disclosed nitrogen-containing compounds will generate the particles 316 shown in FIG. 1c.

FIG. 1d is a cross-sectional side view of the exemplary layers in the 3D NAND stack showing selective etching of SiN exposed on the sidewall in the 3D NAND stack after etching. The SiN exposed sidewall in stack 400 may be etched selectively as shown in FIG. 1d by using the disclosed nitrogen containing compounds to selectively break Si—N bond in SiN layers 404b over Si—O bond in SiO layers 404a forming a selective sidewall SiN etch 416 on the stack of SiO/SiN layers 404 in the via 414. The difference between FIG. 1d and FIG. 1b is in FIG. 1d SiN exposed on the alternative SiO/SiN sidewall is selectively etched by the disclosed nitrogen containing compounds forming the selective sidewall SiN etch 416. Typically, the selective sidewall SiN etch 416 is performed by wet etching using mixtures with phosphoric acid. Replacing wet etch process with dry plasma etch processes is known to greatly improve the economics of semiconductor device fabrication process since wet etching requires moving the substrate to different wet etching equipments. With the disclosed methods, all etching including selective sidewall SiN etch may be performed in one etch equipment, which may reduce the cost of the semiconductor fabrication.

Figure 2:
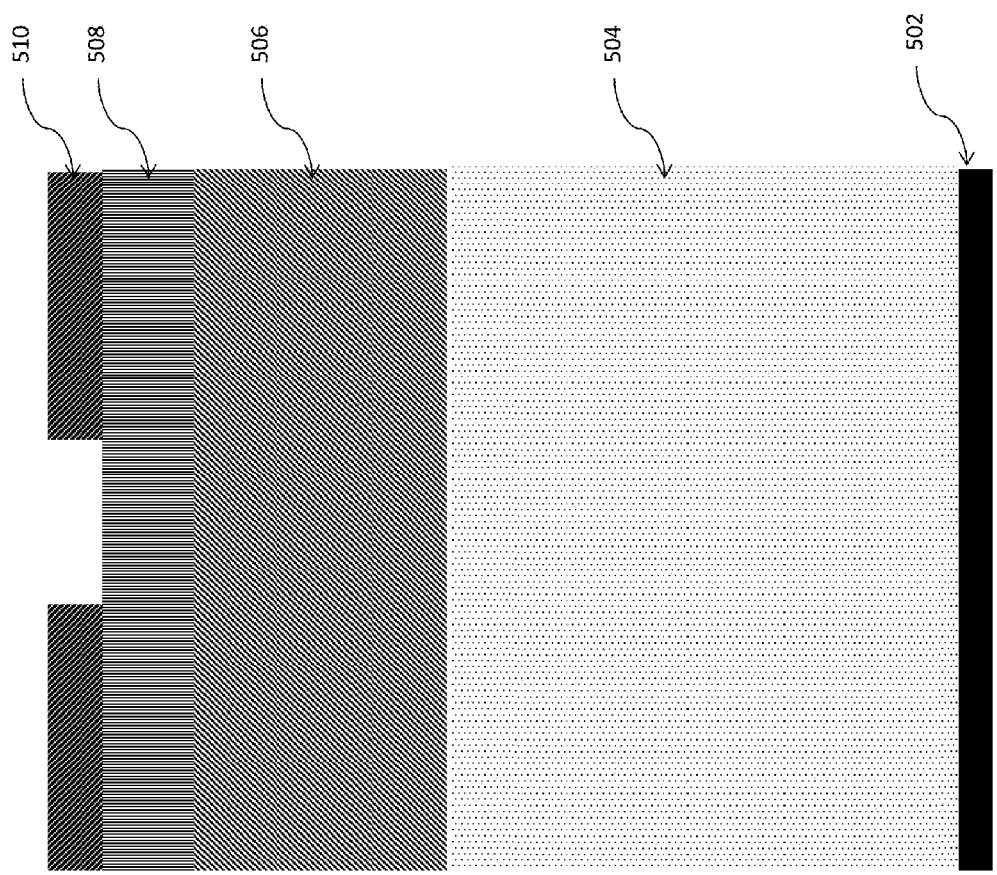
FIG. 2 is an exemplary cross-sectional side view of exemplary layers in a DRAM stack to produce a DRAM memory.

In alternative embodiment, substrate 500 may include a stack of multiple layers thereon as shown in FIG. 2. FIG. 2 is a cross-sectional side view of exemplary layers in a DRAM stack to produce a DRAM memory. In FIG. 2, a stack of four layers is located on top of a silicon wafer 502. An a-C mask layer 506 is located on top of a large SiO layer 504. An antireflective coating layer 508 is located on top of the a-C mask 506. A pattern photoresist layer 510 is located on top of the antireflective coating 508. Herein, a SiON layer (not shown) may be present between the antireflective coating layer 508 and the a-C mask layer 506 to transfer pattern in photoresist layer 510 to the a-C layer 506. One of ordinary skill in the art will recognize that the stack of layers in FIG. 2 is provided for exemplary purposes only and that the disclosed nitrogen-containing etching compounds may be used to etch other stacks of layers, for example, for a stack where the a-C mask layer 506 is replaced with a TiN layer. Furthermore, one of ordinary skill in the art will recognize that the number of layers in the stack may vary (i.e., may include more or less than the layers depicted).

Figure 3B:
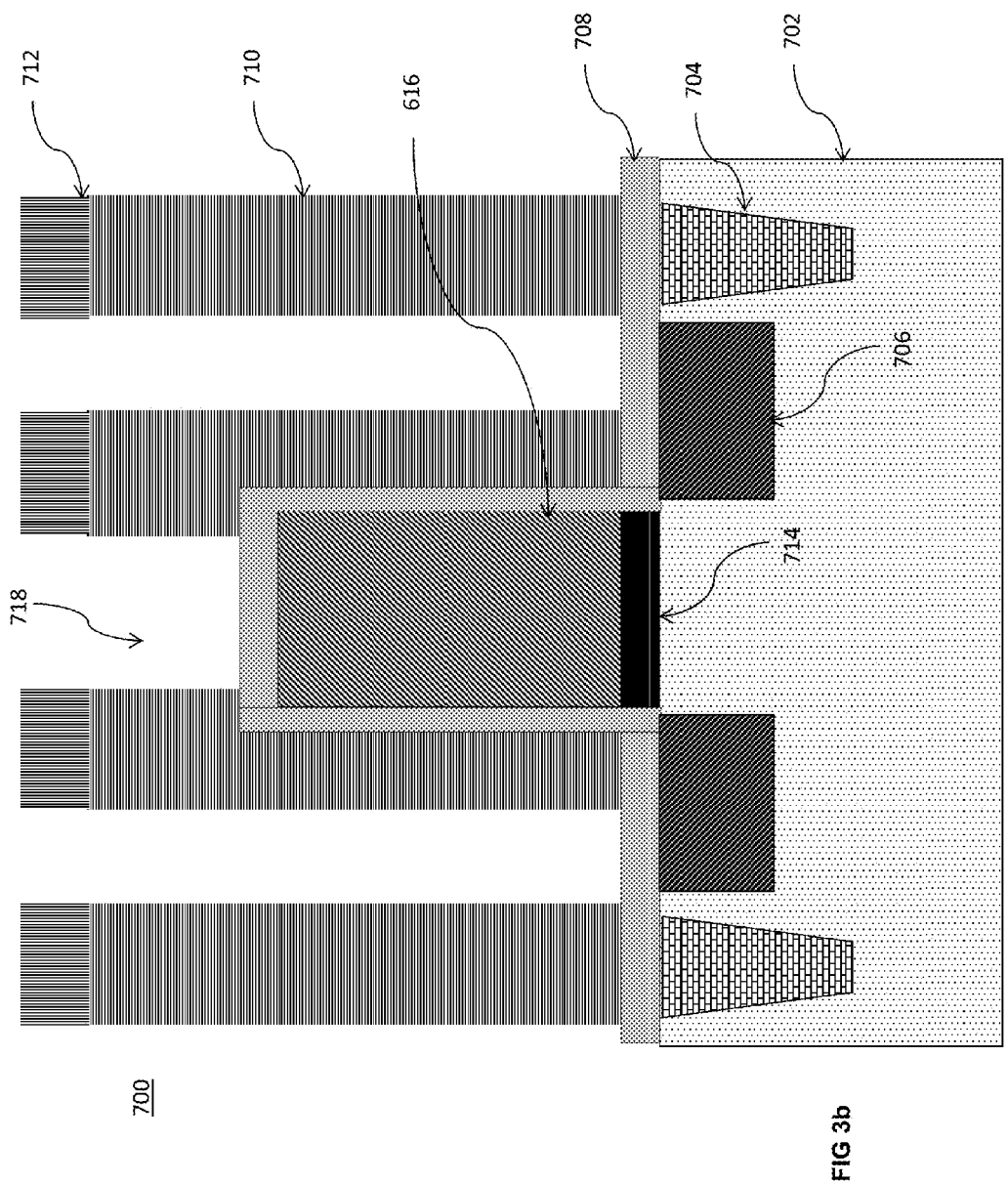
FIG. 3b is an exemplary cross-sectional side view of the exemplary layers of FIG. 3a after etching SiO insulation layer.

FIG. 3a is a cross-sectional side view of exemplary layers showing photoresist pattern over SiO insulation layer surrounding a typical transistor device region to produce a transistor structure. Substrate 600 may include a stack of four layers surrounding a transistor gate electrode region supported on the Silicon wafer 602 as shown in FIG. 3a. The transistor region shown in FIG. 3a includes two doped silicon regions 606 acting as source and drain. Transistor gate dielectric 614 is present underneath gate electrode 616. The whole transistor, i.e., transistor gate dielectric 614 and gate electrode 616, is surrounded by a thin SiN layer 608 which may later act as etch stop layer during contact etch. Each transistor device region 616/606 is separated by SiO isolation regions 604 in the silicon wafer 602 to minimize electrical interference. One of ordinary skill in the art will recognize that layer 602 may be located on top of a silicon oxide layer of the Silicon on Insulator (SOI) wafer. Another SiO layer 610 is deposited on the transistor and used to insulate metal contact to the transistor device regions 606. Photoresist mask 612 is used to pattern the SiO layer 610. Etching is performed using the disclosed nitrogen-containing etching compounds in plasma environment. Herein, photoresist serves as a mask to etch the SiO layer 610 and etching is stopped on the SiN layer 608 as shown in FIG. 3b.

FIG. 3b is across-sectional side view of the exemplary layers of FIG. 3a after etching the SiO insulation layer. The difference between FIG. 3b and FIG. 3a is in FIG. 3b vias 718 are formed in the SiO layer 710 through etching by the disclosed nitrogen-containing compounds. The SiO layer 710 may be etched with photoresist layer 712 as a mask layer. The mask layer may be any suitable photoresist mask materials, such as TiN, a-C and so on. The etching may be stopped at the underlying SiN layer 708.

The disclosed nitrogen-containing etching compounds may also be used to etch the SiN layer 708 underneath with different plasma conditions and different mixtures. One of ordinary skill in the art will recognize that the stack and geometry of layers in FIG. 3a and FIG. 3b is provided for exemplary purposes only and that the disclosed nitrogen-containing etching compounds may be used to etch other types of stacks of layers. Furthermore, one of ordinary skill in the art will recognize that the number of layers in the stack may vary (i.e., may include more or less than the four layers depicted).

The vapor of the disclosed nitrogen-containing etching compounds is introduced into the reaction chamber containing the substrate and silicon-containing films. The vapor may be introduced to the chamber at a flow rate ranging from approximately 0.1 sccm to approximately 1 slm. For example, for a 200 mm wafer size, the vapor may be introduced to the chamber at a flow rate ranging from approximately 5 sccm to approximately 50 sccm. Alternatively, for a 450 mm wafer size, the vapor may be introduced to the chamber at a flow rate ranging from approximately 25 sccm to approximately 250 sccm. One of ordinary skill in the art will recognize that the flow rate may vary from tool to tool.

The disclosed nitrogen-containing etching compounds may be supplied either in neat form or in a blend with an inert gas, such as $N_2$, Ar, He, Xe, etc, or solvent. The disclosed nitrogen-containing etching compounds may be present in varying concentrations in the blend. For liquid nitrogen-containing compounds, the vapor form of the nitrogen-containing etching compounds may be produced by vaporizing the neat or blended nitrogen-containing etching compound solution through a conventional vaporization step such as direct vaporization or by bubbling. The neat or blended nitrogen-containing etching compounds may be fed in liquid state to a vaporizer where it is vaporized before it is introduced into the reactor.

Alternatively, the neat or blended nitrogen-containing etching compounds may be vaporized by passing a carrier gas into a container containing the disclosed nitrogen-containing etching compounds or by bubbling the carrier gas into the disclosed nitrogen-containing compounds. The carrier gas may include, but is not limited to, Ar, He, $N_2$, and mixtures thereof. Bubbling with a carrier gas may also remove any dissolved oxygen present in the neat or blended nitrogen-containing etching compounds solution. The carrier gas and disclosed nitrogen-containing etching compounds are then introduced into the reactor as a vapor.

If necessary, the container containing the disclosed nitrogen-containing etching compounds may be heated to a temperature that permits the nitrogen-containing etching compounds to be in liquid phase and to have a sufficient vapor pressure for delivery into an etching tool. The container may be maintained at temperatures in the range of, for example, approximately 0° C. to approximately 150° C., preferably from approximately 25° C. to approximately 100° C., more preferably from approximately 25° C. to approximately 50° C. More preferably, the container is maintained at room temperature (approximately 25° C.) in order to avoid heating lines to the etch tool. Those skilled in the art recognize that the temperature of the container may be adjusted in a known manner to control the amount of nitrogen-containing compound vaporized.

Additionally, the nitrogen-containing etching compounds are delivered in purity ranging from 95% to 99.999% by volume or could be purified with known standard purification techniques for removal of CO, $CO_2$, $N_2$, $H_2O$, HF, $H_2S$, $SO_2$, halides, and other hydrocarbons or hydrohalocarbons.

An inert gas is also introduced into the reaction chamber in order to sustain the plasma. The inert gas may be He, Ar, Xe, Kr, Ne, $N_2$ or combinations thereof. The etching gas and the inert gas may be mixed prior to introduction to the chamber, with the inert gas comprising between approximately 0.01% v/v and approximately 99.9% v/v of the resulting mixture. Alternatively, the inert gas may be introduced to the chamber continuously while the etching gas is introduced to the chamber in pulses.

The vapor of the disclosed etching gas and inert gas are activated by plasma to produce an activated etching gas. The plasma decomposes the etching gas into radical form (i.e., the activated etching gas). The plasma may be generated by applying RF or DC power. The plasma may be generated with a RF power ranging from about 25 W to about 10,000 W. The plasma may be generated remotely or within the reactor itself. The plasma may be generated in dual CCP or ICP mode with RF applied at both electrodes. RF frequency of plasma may range from 200 KHz to 1 GHz. Different RF sources at different frequency may be coupled and applied at same electrode. Plasma RF pulsing may be further used to control molecule fragmentation and reaction at substrate. One of skill in the art will recognize methods and apparatus suitable for such plasma treatment.

Quadrupole mass spectrometer (QMS), optical emission spectrometer, FTIR, or other radical/ion measurement tools may measure the activated etching gas from the chamber exhaust to determine the types and numbers of species produced. If necessary, the flow rate of the etching gas and/or the inert gas may be adjusted to increase or decrease the number of radical species produced.

The disclosed etching gases may be mixed with other gases either prior to introduction into the reaction chamber or inside the reaction chamber. Preferably, the gases may be mixed prior to introduction to the chamber in order to provide a uniform concentration of the entering gas.

In another alternative, the vapor of the nitrogen-containing compound may be introduced into the chamber independently of the other gases such as when two or more of the gases react.

In another alternative, the etching gas and the inert gas are the only two gases that are used during the etching process.

Exemplary other gases include, without limitation, oxidizers such as $O_2$, $O_3$, CO, $CO_2$, NO, $N_2O$, $NO_2$, and combinations thereof. The disclosed etching gases and the oxidizer may be mixed together prior to introduction into the reaction chamber.

Alternatively, the oxidizer may be introduced continuously into the chamber and the etching gas introduced into the chamber in pulses. The oxidizer may comprise between approximately 0.01% v/v to approximately 99.99% v/v of the mixture introduced into the chamber (with 99.99% v/v representing introduction of almost pure oxidizer for the continuous introduction alternative).

Other exemplary gases with which the etching gas may be mixed include additional etching gases, such as $cC_4F_8$, $C_4F_8$, $C_4F_6$, $CF_4$, $CH_3F$, $CF_3H$, $CH_2F_2$, COS, $CS_2$, $CF_3I$, $C_2F_3I$, $C_2F_5I$, $SO_2$, trans-1,1,1,4,4,4-hexafluoro-2-butene (trans-$C_4H_2F_6$), cis-1,1,1,4,4,4-hexafluoro-2-butene (cis-$C_4H_2F_6$), hexafluoroisobutene ($C_4H_2F_6$), trans-1,1,2,2,3,4-hexafluorocyclobutane (trans-$C_4H_2F_6$), 1,1,2,2,3-pentafluorocyclobutane ($C_4H_3F_5$), 1,1,2,2-tetrafluorocyclobutane ($C_4H_4F_4$), or cis-1,1,2,2,3,4-hexafluorocyclobutane (cis-$C_4H_2F_6$).

The vapor of the etching gas and the additional gas may be mixed prior to introduction to the reaction chamber. The additional etching gas may comprise between approximately 0.01% v/v to approximately 99.99% v/v of the mixture introduced into the chamber.

In one non-limiting exemplary plasma etch process, the vapor of 2,3,3,3-Tetrafluoropropionitrile is introduced into a 200 mm Dual CCP plasma etch tool using a controlled gas flow device. The controlled gas flow device may be a mass flow controller or a bubbler design with inert gas flow to deliver the vapor of the desired molecule. In case of high boiling point molecules, a special low pressure drop mass flow controller from Brooks Automation (No. GF120XSD), MKS Instruments, etc., may be used. The pressure of the reaction chamber is set at approximately 30 mTorr. No gas source heating is necessary, as the vapor pressure of 2,3,3,3-Tetrafluoropropionitrile is approximately 498 torr at room temperature. The distance between the two CCP electrodes is kept at 1.35 cm and the top electrode RF power is fixed at 750 W. The bottom electrode RF power is varied to analyze the performance of the molecule. The reaction chamber contains a substrate having silicon-containing films thereon, similar to those shown in FIG. 1a. The antireflective coating layer 108 is patterned/etched by a fluorocarbon (e.g., $CF_4$ and $CH_2F_2$) and oxygen-containing gas (e.g., $O_2$). The amorphous carbon mask layer is patterned/etched by an oxygen-containing gas. The SiO and SiN layers 104 are patterned by the plasma of the disclosed nitrogen containing organofluorine compounds (e.g., 2,3,3,3-Tetrafluoropropionitrile) and Argon. Argon is independently introduced into the chamber at a 250 sccm flow rate. 2,3,3,3-Tetrafluoropropionitrile is independently introduced into the chamber at 15 sccm. $O_2$ is independently introduced into the chamber and varied from 0 sccm to 20 sccm to determine optimum etching conditions. An aperture having an aspect ratio equal to or greater than 30:1 is produced, which may be used as a channel hole in vertical NAND. Similar example may be used for other stack layers as shown in FIGS. 2 and 3a.

In another non-limiting exemplary plasma etch process, difluoroacetonitrile is introduced into a 200 mm Dual CCP plasma etch tool using a controlled gas flow device. The controlled gas flow device may be a mass flow controller. In case of high boiling point molecules, a special low pressure drop mass flow controller from BrooksAutomation (No. GF120XSD), MKS Instruments, etc., may be used. The pressure of the reaction chamber is set at approximately 30 mTorr. No gas source heating is necessary, as the vapor pressure of difluoroacetonitrile is approximately 900 Torr at 20° C. The distance between the two CCP electrodes is kept at 1.35 cm and the top electrode RF power is fixed at 750 W. The bottom electrode RF power is varied to analyze the performance of difluoroacetonitrile. The reaction chamber contains a substrate 500 having a thick SiO layer 504 thereon, similar to the layer shown in FIG. 2. Prior to this process, the antireflective coating layer 508 is removed by a fluorocarbon (e.g., $CF_4$) and oxygen-containing gas (e.g., $O_2$) and the A-c mask layer 506 is removed by an oxygen-containing gas. Argon is independently introduced into the chamber at a 250 sccm flow rate. Difluoroacetonitrile is independently introduced into the chamber at 15 sccm. $O_2$ is independently introduced into the chamber at 0-20 sccm to determine optimum etching conditions. An aperture having an aspect ratio equal to or greater than 10:1 is produced, which may be used as a contact hole in DRAM. Similar examples may be used for other stack layers as shown in FIGS. 1a and 3a.

The silicon-containing films and the activated etching gas react to form volatile by-products that are removed from the reaction chamber. The a-C mask, antireflective coating, and photoresist layer are less reactive with the activated etching gas. Thus, the activated etching gas selectively reacts with the silicon-containing films to form volatile by-products.

The temperature and the pressure within the reaction chamber are held at conditions suitable for the silicon-containing film to react with the activated etching gas. For instance, the pressure in the chamber may be held between approximately 0.1 mTorr and approximately 1000 Torr, preferably between approximately 1 mTorr and approximately 10 Torr, more preferably between approximately 10 mTorr and approximately 1 Torr, and more preferably between approximately 10 mTorr and approximately 100 mTorr, as required by the etching parameters. Likewise, the substrate temperature in the chamber may range between about approximately −196° C. to approximately 500° C., preferably between approximately −120° C. to approximately 300° C., more preferably between approximately −100° C. to approximately 50° C.; and more preferably between approximately −10° C. to approximately 40° C. Chamber wall temperatures may range from approximately −196° C. to approximately 300° C. depending on the process requirements.

The reactions between the silicon-containing film and the activated etching gas result in anisotropic removal of the silicon-containing films from the substrate. Atoms of nitrogen, oxygen, and/or carbon may also be present in the silicon-containing film. The removal is due to a physical sputtering of silicon-containing film from plasma ions (accelerated by the plasma) and/or by chemical reaction of plasma species to convert Si to volatile species, such as $SiF_x$, wherein x ranges from 1-4.

The plasma activated vapor of the disclosed nitrogen-containing etching compounds preferably exhibits high selectivity toward the mask and etches through the alternating layers of SiO and SiN resulting in a vertical etch profile with no bowing or roughness, which is important for 3D NAND applications. Additionally, plasma activated vapor deposits polymer on sidewall to minimize feature profile deformation. For other applications, such as DRAM and 2D NAND, for example, the plasma activated etching gas under different process conditions may selectively etch SiO from SiN. The plasma activated etching gas may selectively etch SiO and/or SiN from mask layers, such as a-C, photoresist, p-Si, or silicon carbide; or from metal contact layers, such as Cu; or from channel regions consisting of SiGe or polysilicon regions.

The disclosed etch processes using the disclosed nitrogen-containing etching compounds as the etching gases produce channel holes, gate trenches, staircase contacts, capacitor holes, contact holes, etc., in the silicon-containing films. The resulting aperture may have an aspect ratio ranging from approximately 10:1 to approximately 200:1 and a diameter ranging from approximately 5 nm to approximately 50 nm. For example, one of ordinary skill in the art will recognize that a channel hole etch produces apertures in the silicon-containing films having an aspect ratio greater than 60:1.

Typical materials that need to be etched may be SiO. A process of etching SiO may be relevant to etching trenches in Borophosphosilicateglass (BPSG), Tetraethylorthosilicate (TEOS), or low deposition rate TEOS (LDTEOS). An etch stop layer may be silicon nitride or silicon oxygen nitride (SiON) or poly silicon. A mask material used may be a-C, p-Si, or photo resist materials. Herein, the disclosed nitrogen-containing etching compounds are applied to etch SiO, SiN, p-Si and/or a-C substrate films.

EXAMPLES

The following non-limiting examples are provided to further illustrate embodiments of the invention. However, the examples are not intended to be all inclusive and are not intended to limit the scope of the inventions described herein.

In the following examples, the etch performance of $C_2HF_2N$, $C_3HF_4N$, and $C_2F_3N$ nitrogen containing compounds are evaluated and compared against $C_5F_5N$ (CAS 700-16-3) and standard gases like $cC_4F_8$ and $C_4F_6$. The results show that $C_2HF_2N$, $C_3HF_4N$, and $C_2F_3N$ nitrogen-containing etching compounds offer sidewall protection and could be used for etching semiconductor structures, such as contact etch.

Herein, the target etching requirements for etchants or etching gases for contact etch are:

1. Etch rates of oxide (i.e., SiO) have to be high;
2. Selectivity of SiO to other materials, typically SiN, should be high;
3. Selectivity of SiO to other materials, typically p-Si or a-C, should be high.

While all the above tested compounds $C_2HF_2N$, $C_3HF_4N$, and $C_2F_3N$ meet certain targets, the results of the compounds $C_3HF_4N$ and $C_2HF_2N$ show greater promise as they meet all the required etching targets for contact etching applications.

Etching experiments were performed on four 1×1 $cm^2$ coupons having four different substrate materials including SiO, SiN, p-Si, and a-C. Deposition and/or etch rates are measured using ellipsometer and/or SEM by measuring the change in etch thickness as a function of etching time. The coupons are placed on 200 mm diameter carrier wafer and held in contact by using double sided carbon tape obtained from 2 spi manufacturer. Alternatively, thermal paste could be used to stick coupons on carrier wafer.

Deposition tests are performed on 1×1 $cm^2$ Si coupon at 30 mTorr, and source power of 750 W (27 MHz), with no bias power at the substrate. The process feed mixture contains 250 sccm of Ar, and 15 sccm of etch gas. The deposition test sample is then sent for XPS analysis to study the type of polymerizing film formed on the substrate.

Etching tests are performed at 30 mTorr, source power of 750 W (27 MHz), and bias power of 1500 W (2 MHz). The feed mixture contains 250 sccm of Ar, 15 sccm of etch gas, while $O_2$ is varied in the range 0 to 15 sccm.

Figure 4:
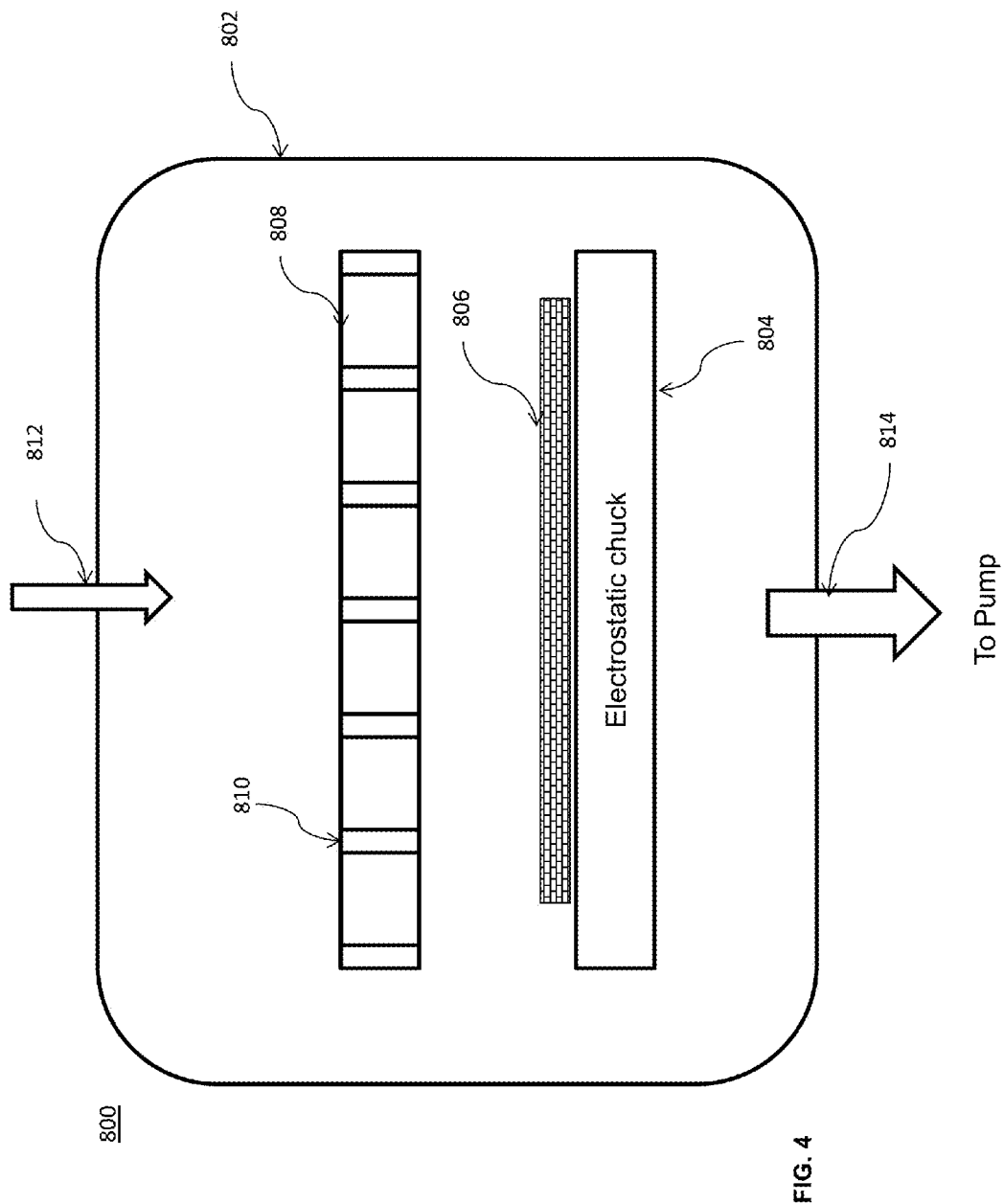
FIG. 4 is a cross-sectional side view of exemplary reactor system applied in deposition and etching tests.

FIG. 4 is an exemplary cross-sectional side view of exemplary reactor system applied in deposition and etching tests. As shown, the reactor 800 includes a reactor chamber 802. Inside of the reactor chamber 802, a wafer 806 attached on the top of a bottom electrode 804 may be placed in the bottom portion of the reactor chamber 802, and a silicon top electrode showerhead 808 may be placed on the top portion of the reactor chamber 802. The bottom electrode 804 may be an electrostatic chuck having bias power applied thereto. For example, 2 MHz RF bias power may be applied to the bottom electrode 804. The wafer 806 may have multi layers that need to be etched. The silicon top electrode showerhead 808 has a plurality of holes 810 in the showerhead through which the gases pass. The gases may be introduced into the reactor chamber 802 through gas inlet 812 and then pass through holes 810 in the showerhead 808 for uniform gas distribution. Source power may be applied to the silicon top electrode showerhead 808. For example, 27 MHz RF source power may be applied to the silicon top electrode showerhead 808. Between the silicon top electrode showerhead 808 and the bottom electrode 804 is the plasma region. The gases passing through the holes 810 in the showerhead 808 may be ionized in the plasma region and then perform etching on the wafer 806. The gases may be removed by pumping the gases out of the reactor chamber 802 from outlet 814.

Additionally, a mass spectrometer may be used to study electron impact ionizations of the etch gases. For this test, the etch gases are allowed to flow through the mass spectrometer chamber and a Quadrupole mass spectrometer (Hiden Analytical Inc.) detector is used to study the fragments from the etch gas as a function of electron energy.

Example 1

Figure 5:
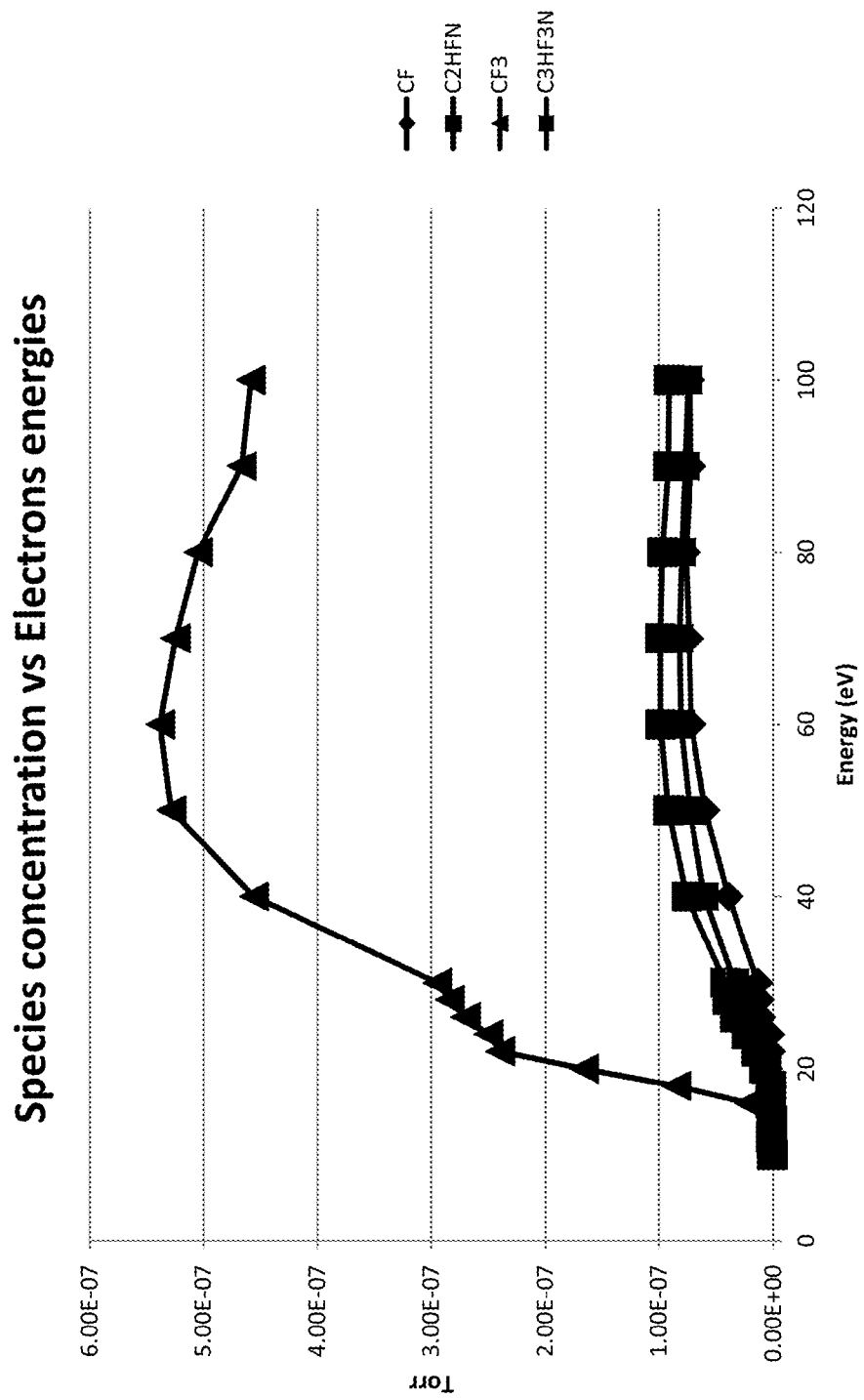
FIG. 5 is a graph demonstrating the electron impact ionization versus energy of $C_3HF_4N$.

FIG. 5 is a graph demonstrating electron impact ionization data for $C_3HF_4N$. In FIG. 5, the x-axis represents electron energy and y-axis represents the partial pressure of the fragment species. FIG. 5 shows that the major fragments for $C_3HF_4N$ are $CF_3$ and $C_2HFN$. The $C_2HFN$ fragment has 1:2 F/C ratios and may readily polymerize upon reaching the substrate.

Example 2

Figure 6:
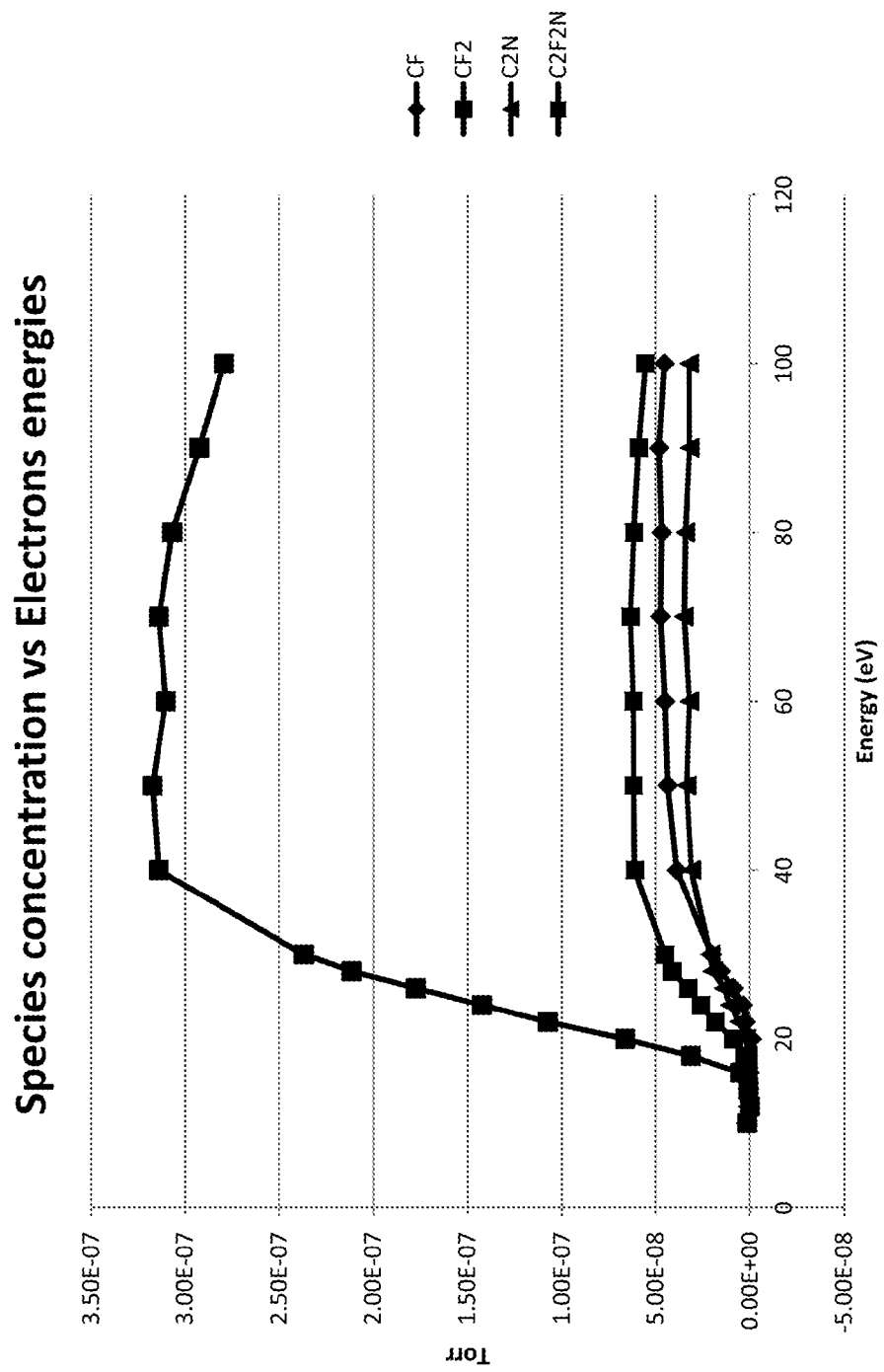
FIG. 6 is a graph demonstrating the electron impact ionization versus energy of $C_2HF_2N$.

FIG. 6 is a graph demonstrating electron impact ionization data for $C_2HF_2N$. In FIG. 6, the x-axis represents electron energy and y-axis represents the partial pressure of the fragment species. FIG. 6 shows that the major fragments for $C_2HF_2N$ are $CF_2$ and $C_2F_2N$. The $C_2F_2N$ fragment has a low F/C ratio and will readily polymerize reaching the substrate.

Example 3

Figure 7:
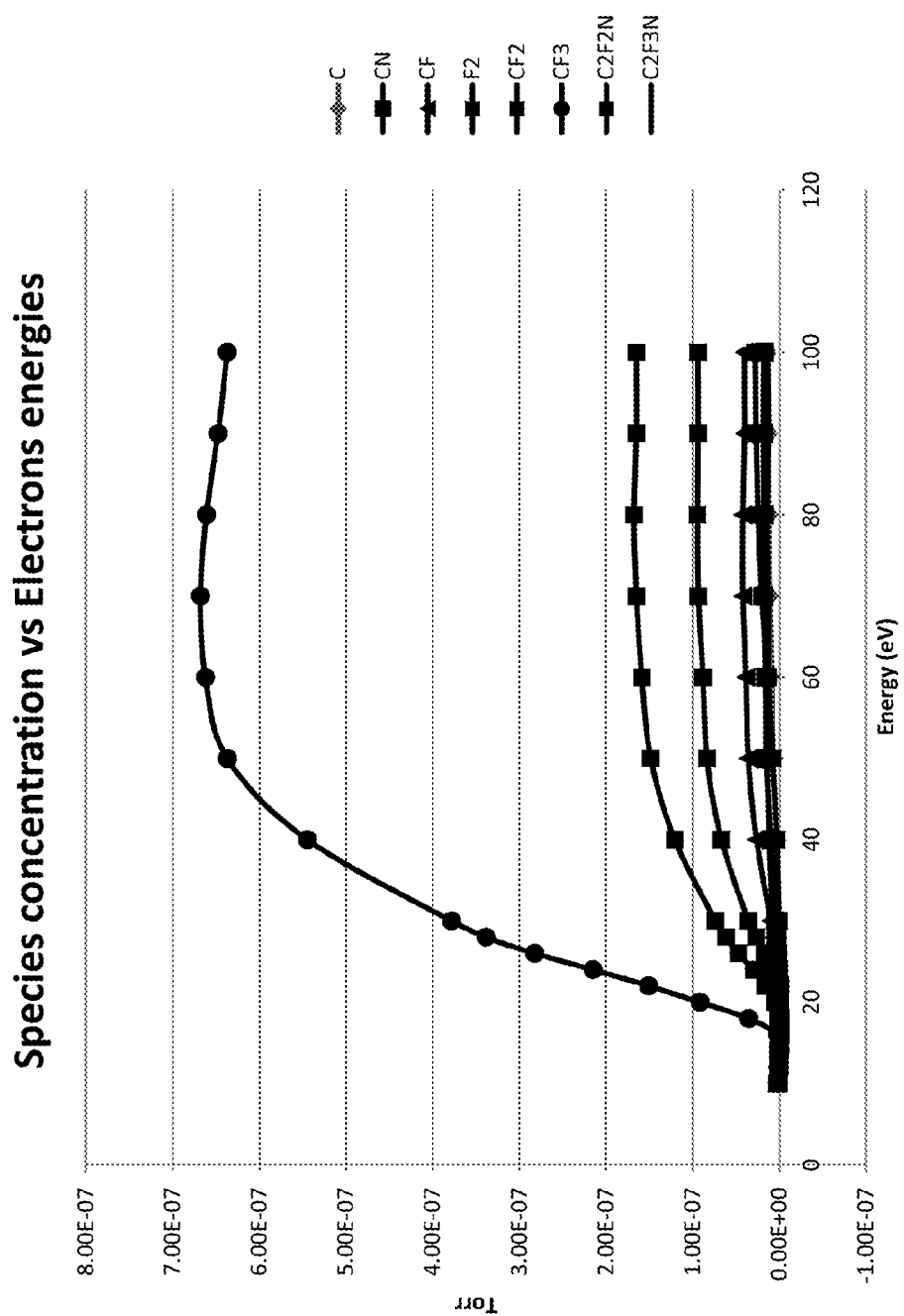
FIG. 7 is a graph demonstrating the electron impact ionization versus energy of $C_2F_3N$.

FIG. 7 is a graph demonstrating electron impact ionization data for $C_2F_3N$. In FIG. 7, the x-axis represents electron energy and y-axis represents the partial pressure of the fragment species. FIG. 7 shows that the major fragments for $C_2F_3N$ are $CF_3$ and $C_2F_2N$. The $C_2F_2N$ fragment has a low F/C ratio and will readily polymerize reaching the substrate.

Example 4

The deposition test is an experiment conducted on a blanket 1×1 cm² Si coupon, where the source power (750 W @ 27 MHz) is applied with no bias power. Because of the absence of bias power, the ions reaching the substrate may not have sufficient energy to etch. In addition, the neutrals and active species reaching the surface stick to the surface, based on their sticking coefficient, and deposit a thin polymer layer. This thin polymer layer may be responsible for sidewall passivation that often provides the selectivity. The deposition test experimental condition helps simulate the polymer layer formed during plasma processing of patterns either on surface or on sidewalls.

When the deposition test has been performed, for 60 sec, at 30 mTorr pressure with process gas mixture containing 250 sccm of Ar and 15 sccm of $C_2F_3N$, a 260 nm polymer film is deposited on Si. The deposition rate is thus 260 nm/min for $C_2F_3N$.

For the same deposition test conditions, it was found that $C_2HF_2N$ yielded deposition rate of 150 nm/min, and $C_3HF_4N$ yielded deposition rate of 190 nm/min. For $C_5F_5N$, the deposition test has been performed, for 60 sec, at 30 mTorr pressure with process gas mixture containing 250 sccm of Ar and 5 sccm of $C_5F_5N$, and it yields deposition rate of 120 nm/min.

Figure 8:
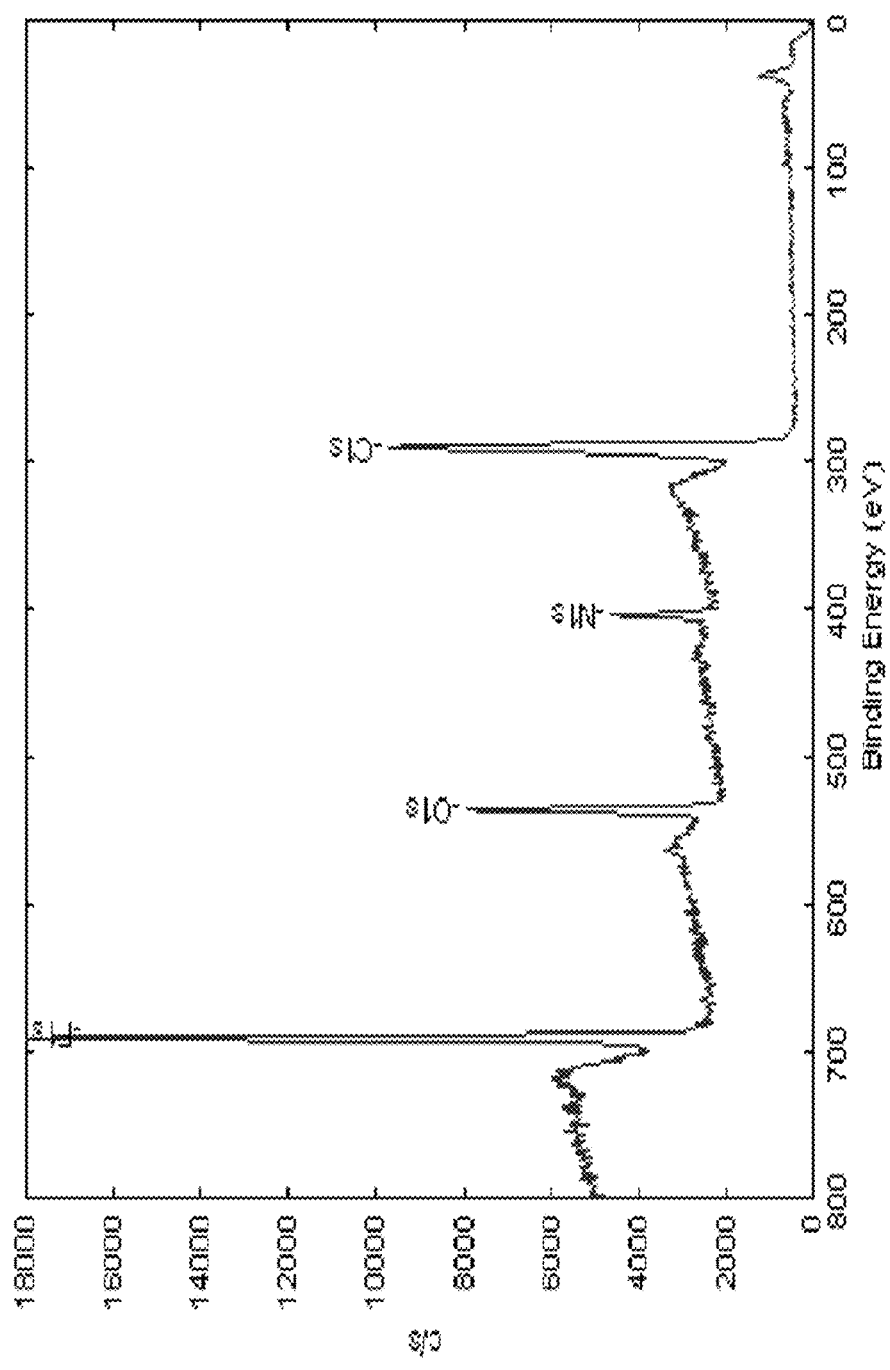
FIG. 8 is a X-ray Photoelectron Spectrometric graph demonstrating the element content of a polymerizing film formed with $C_3HF_4N$ during deposition test.

The sample is further sent for XPS analysis where the nature of the polymerizing layer is investigated. FIG. 8 is a graph providing XPS data of a polymerizing film formed with $C_3HF_4N$ during deposition test. The wide elemental scan from XPS analysis, from FIG. 8, clearly shows the presence of C, F, O, and N peaks, which shows the evidence of Nitrogen present in the polymerizing film. Thus, nitrogen is present in the polymerizing film and it may act as a better sidewall passivation layer and helps create vertical profiles during high aspect ratio etching.

Example 5

Figure 9:
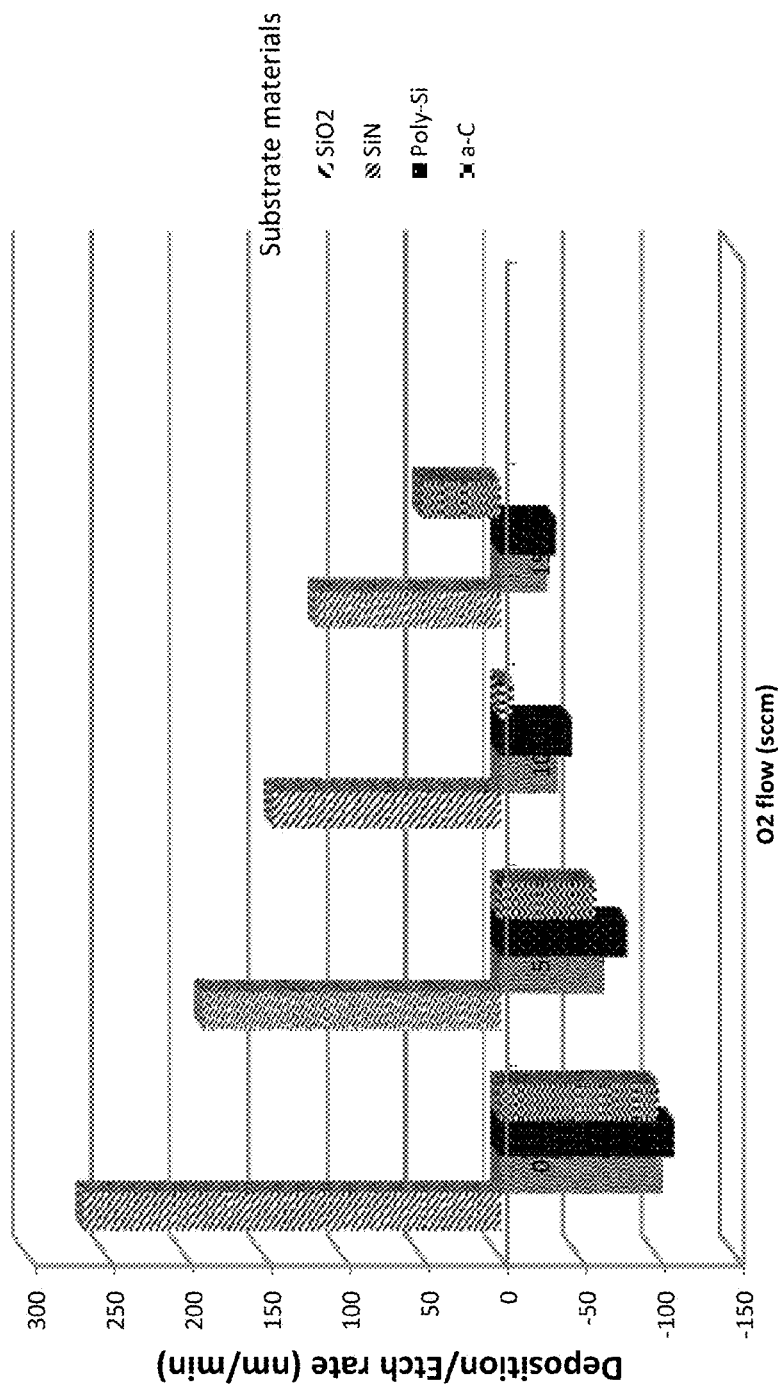
FIG. 9 is a graph demonstrating the deposition or etch rates of SiO, SiN, p-Si and a-C films as a function of oxygen flow rate using $C_2HF_2N$ and $O_2$.

FIG. 9 is a graph demonstrating etch rates of SiO, SiN, p-Si and a-C with $C_2HF_2N$ and $O_2$. In FIG. 9, the positive y-axis represents etch rates while the negative y-axis represents deposition rates; the x-axis is $O_2$ flow rate in sccm; the $C_2HF_2N$ flow rate is fixed at 15 sccm while the $O_2$ flow rate is varied from 0 to 15 sccm.

As shown, when no oxygen is added (0 sccm $O_2$ condition), $C_2HF_2N$ readily etches silicon oxide but does not etch other substrates. This is a very important result as $C_2HF_2N$ etches silicon oxide and protects the other substrate materials offering infinite selectivity of oxide to other substrate materials. Small damage of few nanometer due to plasma ion bombardment is expected before the etch gas starts protecting the other substrate materials. This damage is not characterized and not accounted for in the selectivity measurements. When 5 sccm of oxygen is added to the mixture, the etch rate of silicon oxide decreases compared to the 0 sccm oxygen condition, but $C_2HF_2N$ still deposits on all other substrates preserving the selectivity of Oxide to other substrate materials. When 10 sccm of oxygen is added to the mixture, the etch rate of silicon oxide continues to decrease, but, $C_2HF_2N$ still deposits on all other substrates preserving the selectivity of silicon oxide to other substrate materials. When 15 sccm of oxygen is added to the mixture, while the etch rate of silicon oxide once again decreases, $C_2HF_2N$ still deposits on Nitride and p-Si, and preserves selectivity of silicon oxide to silicon nitride and p-Si. At 15 sccm $O_2$ test condition, etching is observed on a-C and the selectivity of silicon oxide to a-C decreases drastically from infinity to ~2 (i.e., etch rate of SiO/Etch rate of a-C). Overall, $C_2HF_2N$ offers the widest possible range of process conditions that give infinite selectivity to silicon nitride and p-Si substrates. The etch rates of silicon oxide are lower than the standard $cC_4F_8$ gas (which is above 550 nm/min) but may be readily increased by adding an additive gas like $CF_4$, $C_3F_8$, $cC_4F_8$ or $C_4F_6$.

Example 6

Figure 10:
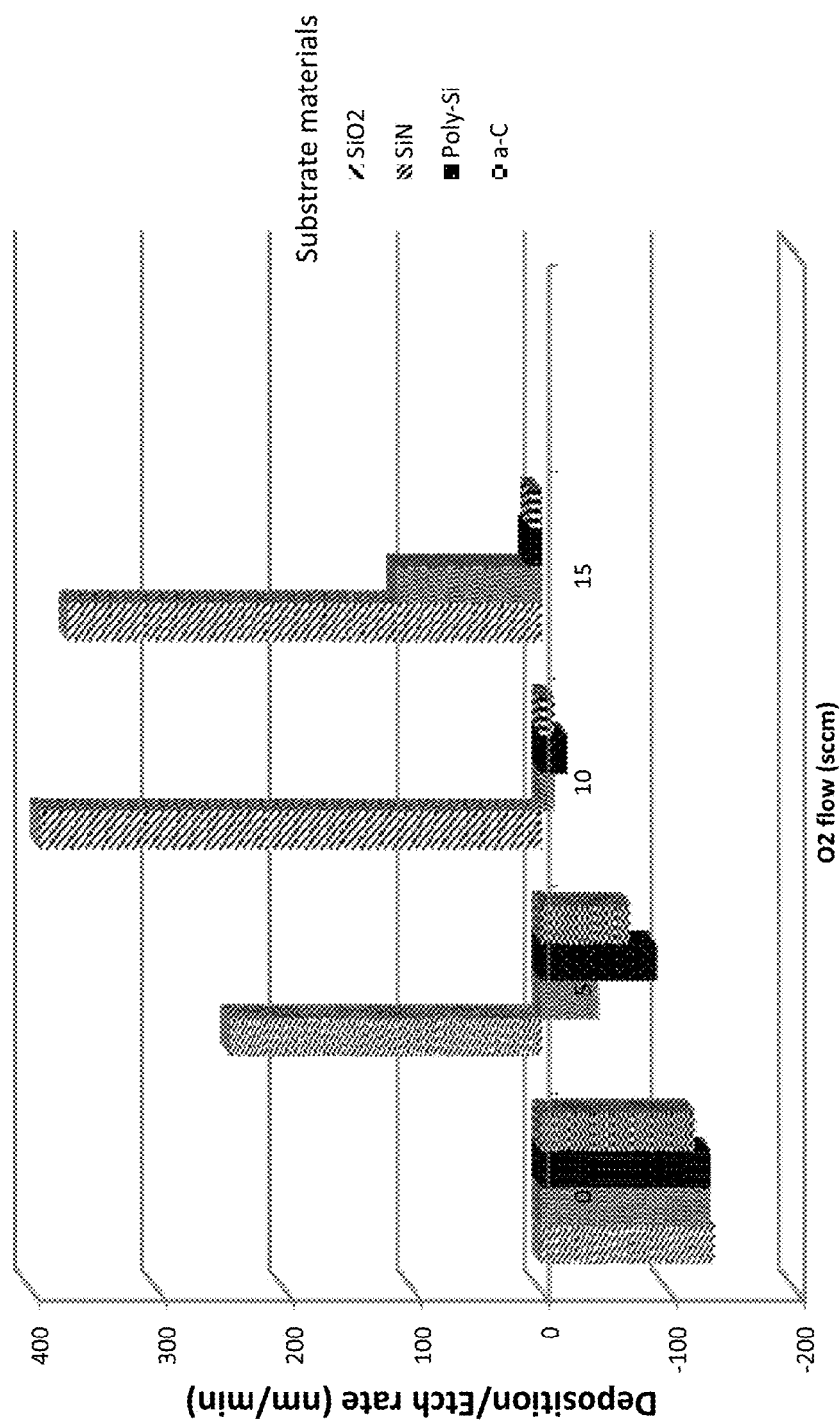
FIG. 10 is a graph demonstrating the deposition or etch rates of SiO, SiN, p-Si and a-C films as a function of oxygen flow rate using $C_3HF_4N$ and $O_2$.

FIG. 10 is a graph demonstrating etch rates of SiO, SiN, p-Si and a-C with $C_3HF_4N$ and $O_2$. In FIG. 10, the positive y-axis represents etch rates while the negative y-axis represents deposition rates; the x-axis is $O_2$ flow rate in sccm; the $C_3HF_4N$ flow rate is fixed at 15 sccm while the $O_2$ flow rate is varied from 0 to 15 sccm.

As shown, when no oxygen is added (0 sccm $O_2$ condition), $C_3HF_4N$ deposits on all substrates. As 5 sccm of oxygen is added to the mixture, $C_3HF_4N$ starts etching silicon oxide but deposits on all the other substrate materials offering infinite selectivity of silicon oxide to the other substrate materials. Similar behavior is seen at 10 sccm of $O_2$. When 15 sccm of oxygen is added, $C_3HF_4N$ starts etching silicon nitride and the selectivity to silicon nitride drops to ~3 (i.e., etch rate of SiO/Etch rate of SiN) while still maintaining high selectivity of ~40 to a-C.

Example 7

Figure 11:
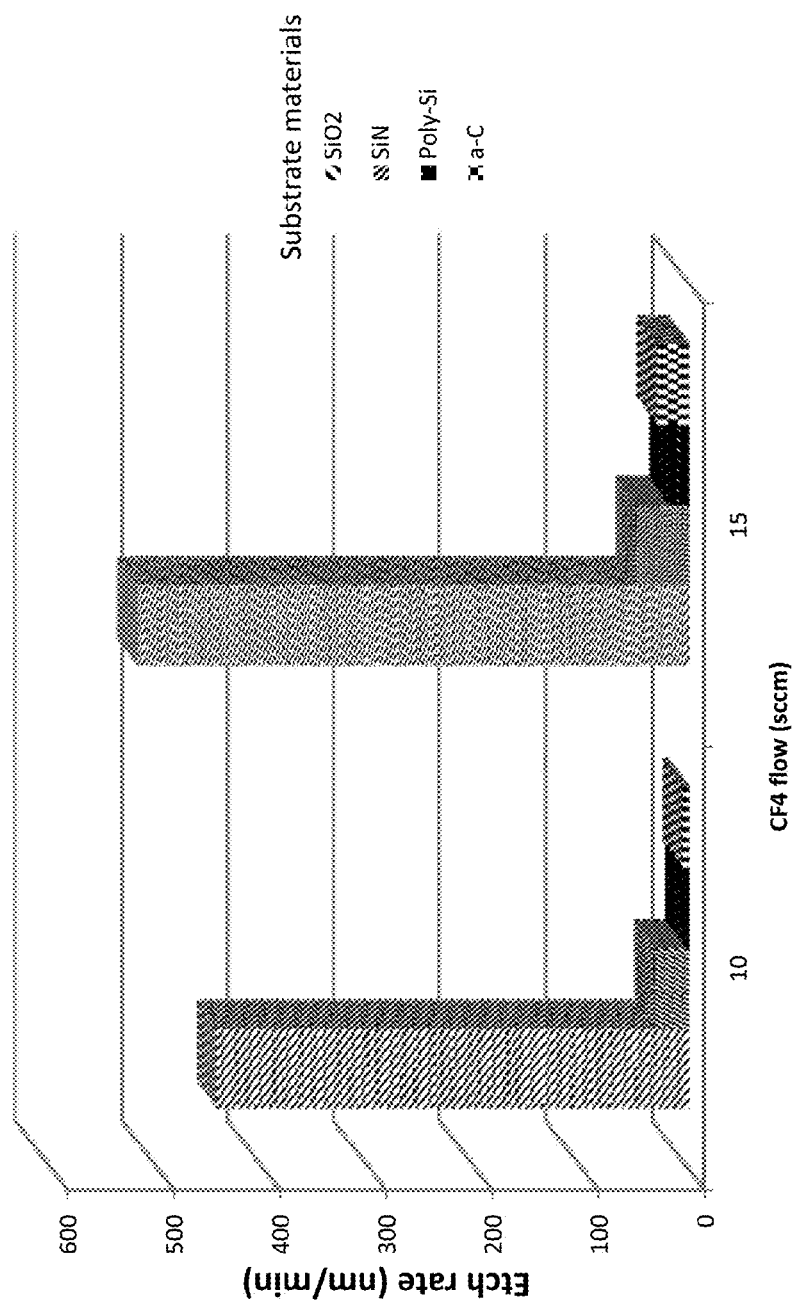
FIG. 11 is a graph demonstrating etch rates of SiO, SiN, p-Si and a-C films as a function of oxygen flow rate using $C_3HF_4N$ and $CF_4$.

FIG. 11 is a graph demonstrating etch rates of SiO, SiN, p-Si and a-C with $C_3HF_4N$ and $CF_4$. In FIG. 11, the positive y-axis represents etch rates while the negative y-axis represents deposition rates; the x-axis is $CF_4$ flow in sccm; the $C_3HF_4N$ flow rate is fixed at 15 sccm, the $O_2$ flow rate is fixed at 5 sccm, while the $CF_4$ flow rate is varied from 10 to 15 sccm.

Figure 12:
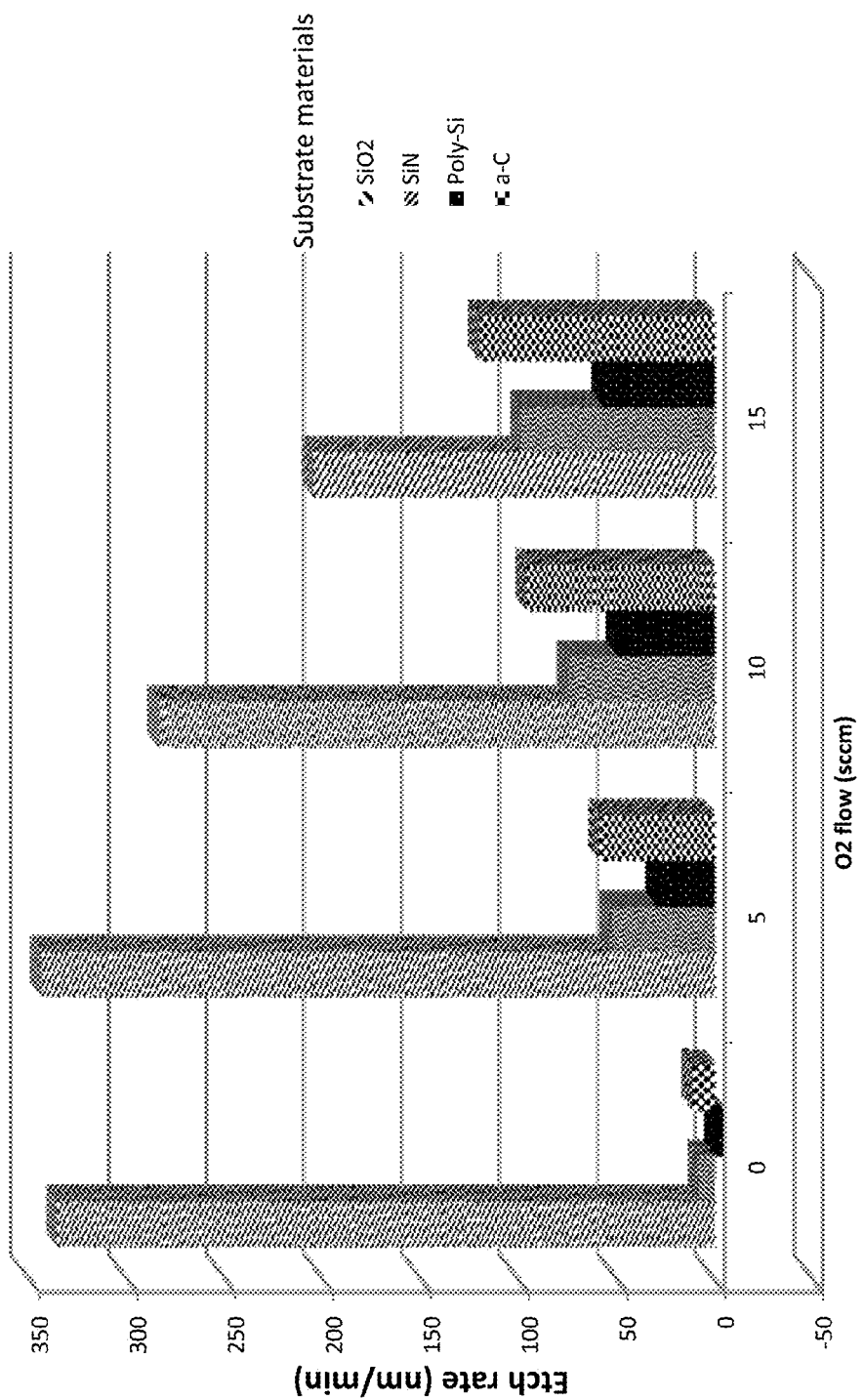
FIG. 12 is a graph demonstrating etch rates of SiO, SiN, p-Si and a-C films as a function of oxygen flow rates using $C_2F_3N$ and $O_2$.

In order to enhance the etch rates of SiO, comparable to the performance of $cC_4F_8$ (see comparative examples below), $CF_4$ is added to the etch gas mixture of 250 sccm Ar and 15 sccm $C_3HF_4N$. FIG. 12 is a graph demonstrating that by adding $CF_4$ to the process gas mixture, the etch rates of SiO have increased up to 500 nm/min while maintaining good selectivity to p-Si and a-C. Additives like $C_xF_{2x+2}$ (x=1 to 5), $C_xF_{2x}$ (x=3 to 5), $C_xF_{2x-2}$ (x=4 to 5) may be added to the mixture to enhance Oxide etch rate.

Example 8

FIG. 12 is a graph demonstrating etch rates of SiO, SiN, p-Si and a-C with $C_2F_3N$ and $O_2$. In FIG. 12, the positive y-axis represents etch rates while the negative y-axis represents deposition rates; the x-axis is $O_2$ flow in sccm; $C_2F_3N$ flow is fixed at 15 sccm while $O_2$ flow is varied from 0 to 15 sccm.

As shown, when no oxygen is added (0 sccm $O_2$ condition), $C_2F_3N$ readily etches silicon oxide but etches other substrates at a very slow rate. This results in a very high selectivity of ~40 for silicon oxide to silicon nitride and selectivity of ~30 for silicon oxide to a-C and infinite selectivity to p-Si. However, as the oxygen flow rate increased to 5 sccm and beyond, the selectivity slows drops. $C_2F_3N$ is promising and offers better selectivity than standard gases like $cC_4F_8$ or $C_4F_6$ used in industry.

Comparative Example 1

Figure 13:
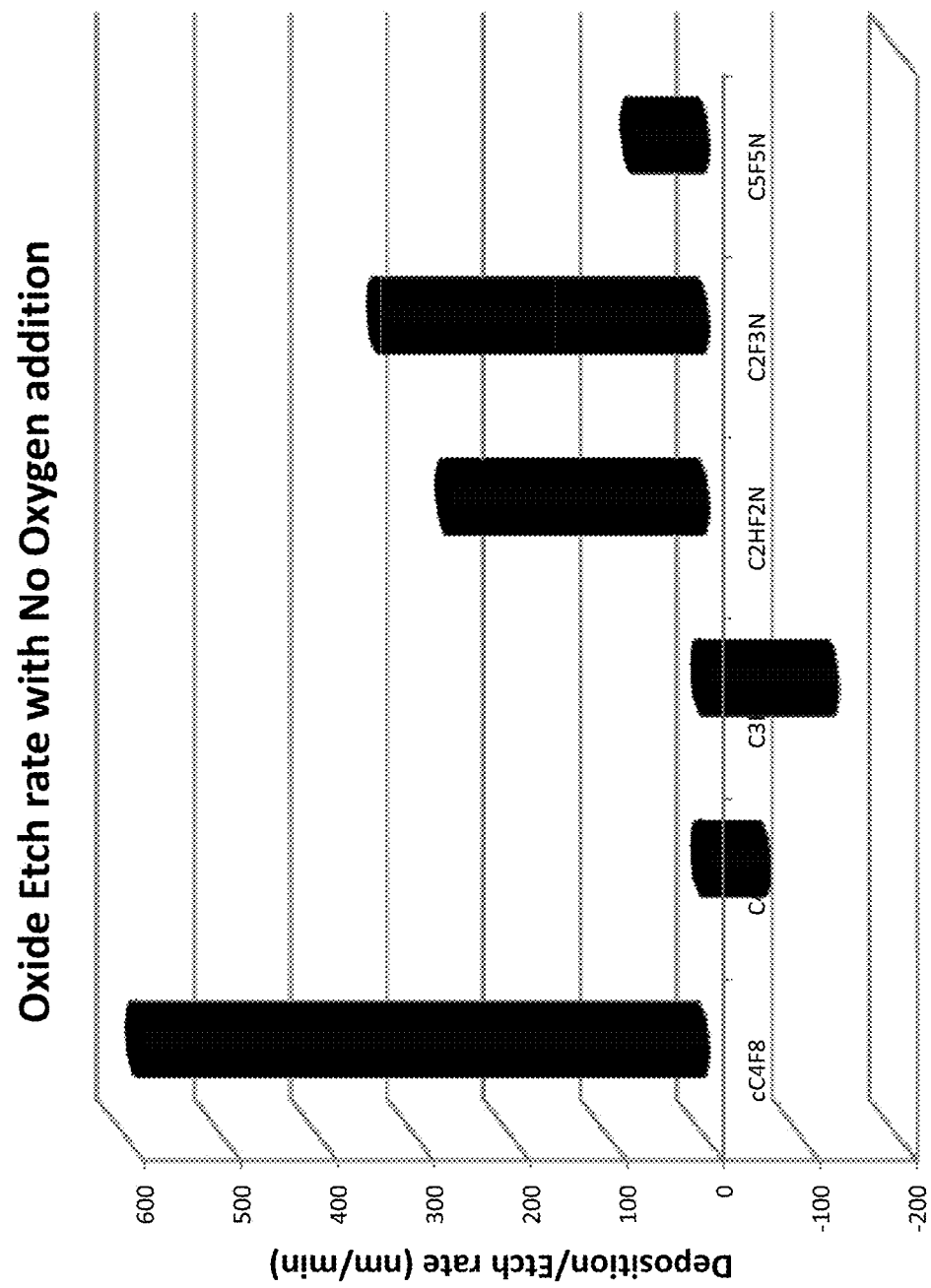
FIG. 13 is a graph comparing the silicon oxide deposition and etch rates without oxygen addition of $C_3HF_4N$, $C_2HF_2N$, $C_5F_5N$, and $C_2F_3N$ with $cC_4F_8$ and $C_4F_6$.

FIG. 13 is a graph demonstrating silicon oxide etch rates of $C_3HF_4N$, $C_2HF_2N$, $C_5F_5N$, and $C_2F_3N$ versus the prior art $cC_4F_8$ and $C_4F_6$ etch gases. In FIG. 13, the positive y-axis represents etch rates while the negative y-axis represents deposition rates; the x-axis represents the compounds to be compared. FIG. 13 shows that the nitrogen containing compounds $C_2HF_2N$ and $C_2F_3N$ have higher etch rates than those of $C_3HF_4N$ and $C_5F_5N$. Thus, nitrogen containing compounds may be designed to obtain better etching performance than commonly used $cC_4F_8$ and $C_4F_6$.

Comparative Example 2

Figure 14:
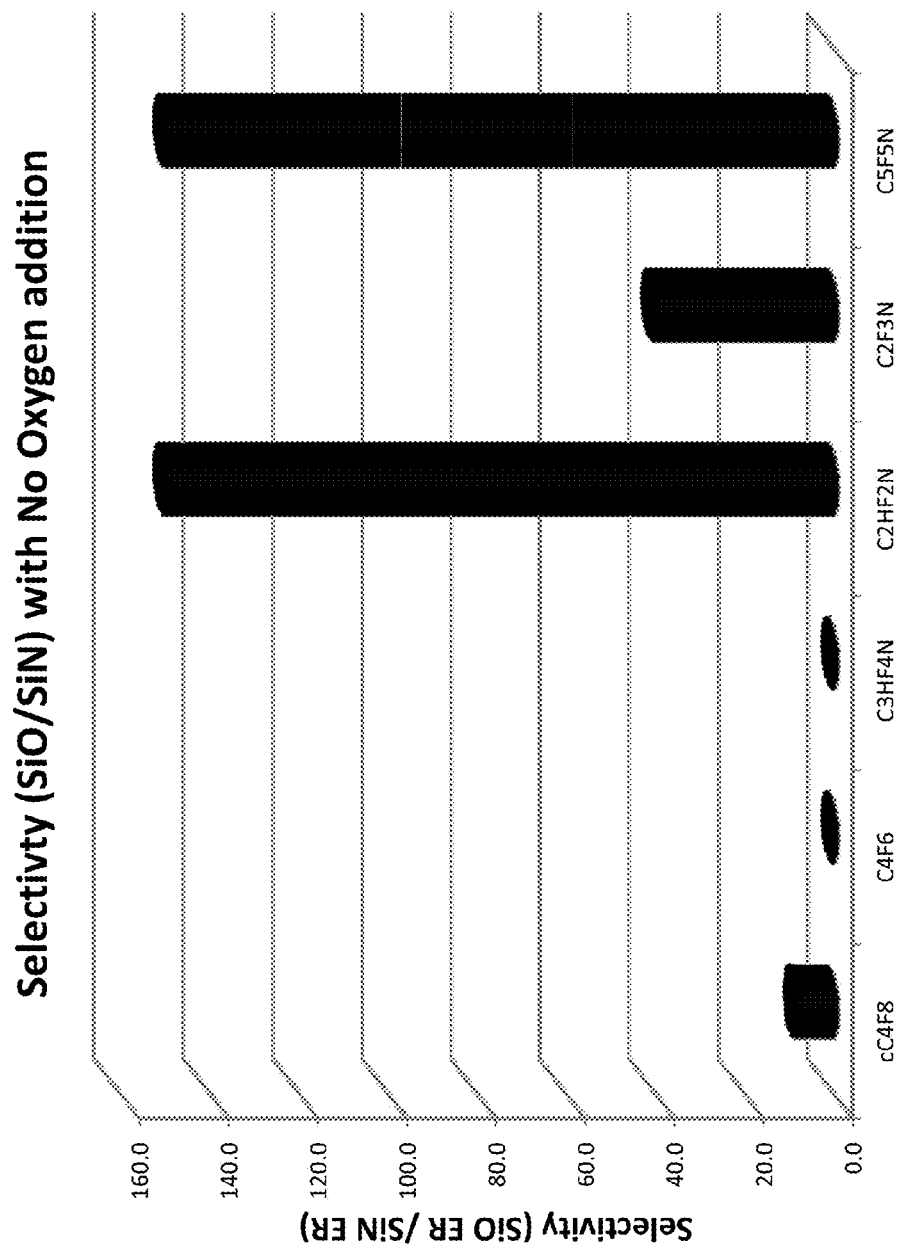
FIG. 14 is a graph comparing the selectivity of silicon oxide to silicon nitride without oxygen addition of $C_3HF_4N$, $C_2HF_2N$, $C_5F_5N$, and $C_2F_3N$ with $cC_4F_8$ and $C_4F_6$.

FIG. 14 is a graph demonstrating selectivity of silicon oxide to silicon nitride with $C_3HF_4N$, $C_2HF_2N$, $C_5F_5N$, and $C_2F_3N$ versus the prior art $cC_4F_8$ and $C_4F_6$ etch gases with no oxygen addition. In FIG. 14, the positive y-axis represents etch rates while the negative y-axis represents deposition rates; the x-axis represents the compounds compared. FIG. 14 shows that $C_2HF_2N$ and $C_5F_5N$ have the infinite selectivity (represented as 150) of silicon oxide to silicon nitride with 0 sccm oxygen addition.

Comparative Example 3

Figure 15:
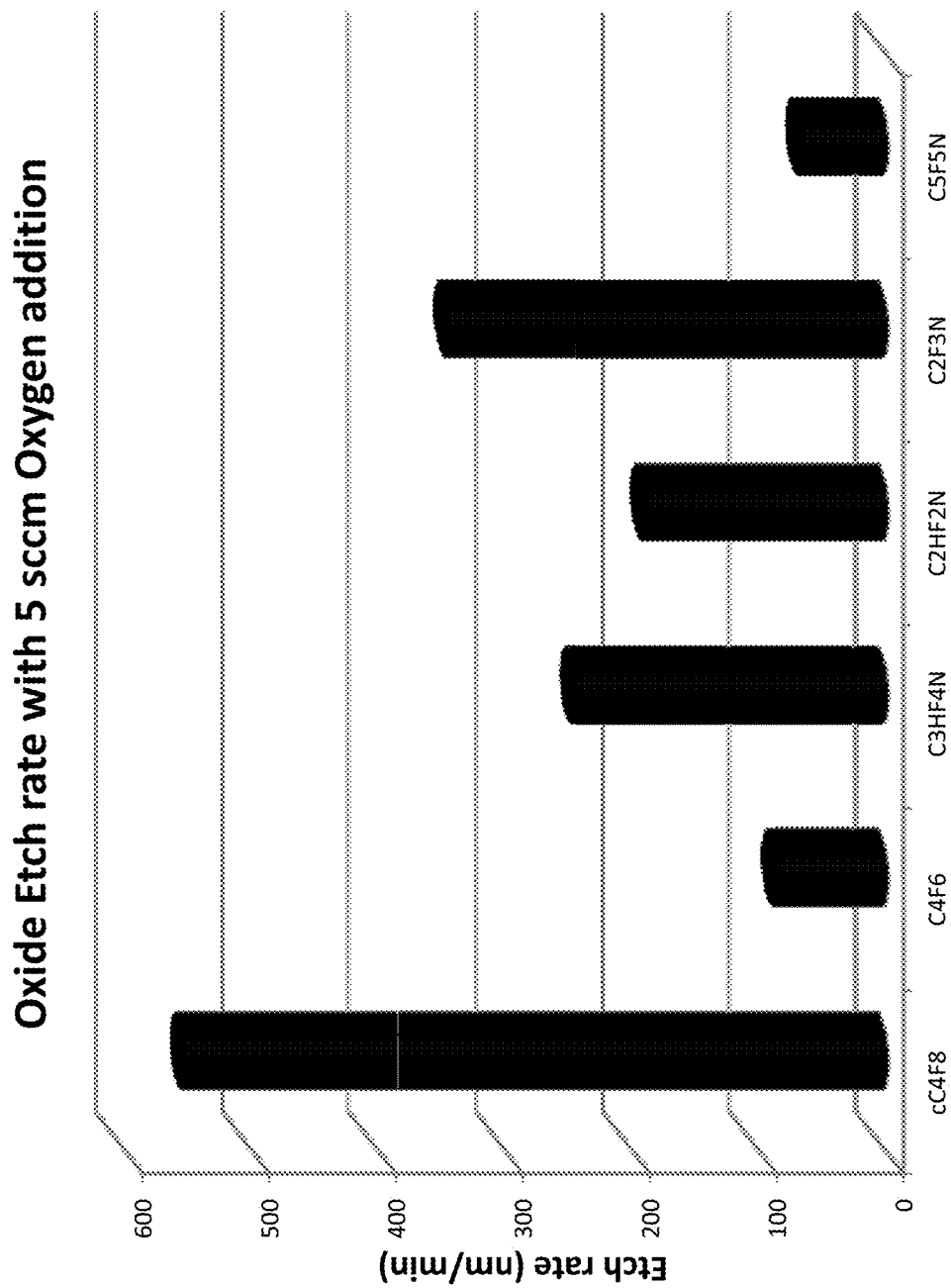
FIG. 15 is a graph comparing the silicon oxide etch rates with 5 sccm oxygen addition of $C_3HF_4N$, $C_2HF_2N$, $C_5F_5N$, and $C_2F_3N$ with $cC_4F_8$ and $C_4F_6$.

FIG. 15 is a graph demonstrating silicon oxide etch rates of $C_3HF_4N$, $C_2HF_2N$, $C_5F_5N$, and $C_2F_3N$ versus the prior art $cC_4F_8$ and $C_4F_6$ etch gases including a 5 sccm oxygen addition. In FIG. 15, the positive y-axis represents etch rates while the negative y-axis represents deposition rates; the x-axis represents the compounds compared. As shown in FIG. 15, the rank of the etching rates with 5 sccm oxygen addition are $cC_4F_8 > C_2F_3N > C_3HF_4N > C_2HF_2N > C_4F_6 > C_5F_5N$.

Comparative Example 4

Figure 16:
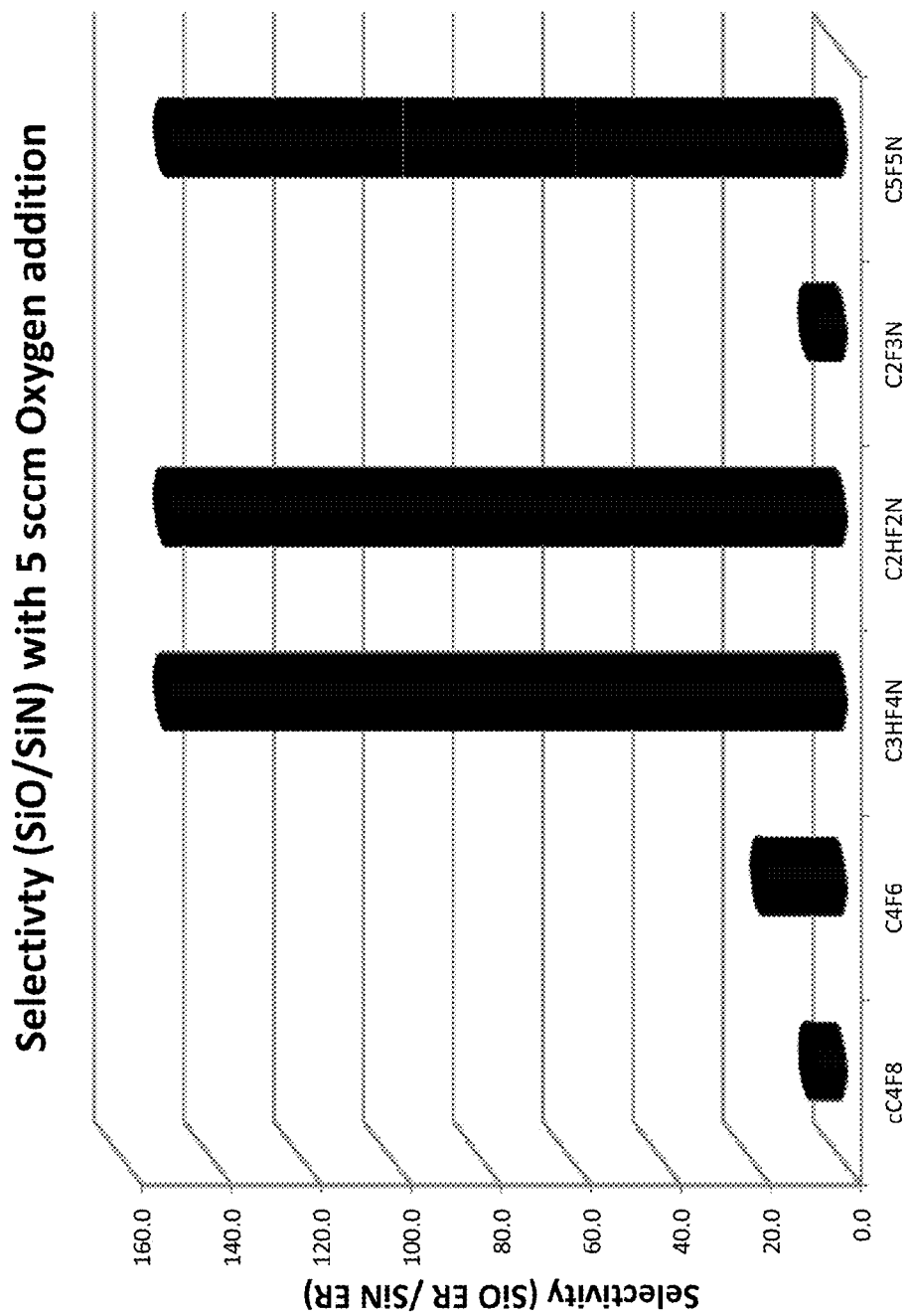
FIG. 16 is a graph comparing the selectivity of silicon oxide to silicon nitride with 5 sccm oxygen addition of $C_3HF_4N$, $C_2HF_2N$, $C_5F_5N$, and $C_2F_3N$ with $cC_4F_8$ and $C_4F_6$.

FIG. 16 is a graph demonstrating selectivity (SiO/SiN) of $C_3HF_4N$, $C_2HF_2N$, $C_5F_5N$, and $C_2F_3N$ versus the prior art $cC_4F_8$ and $C_4F_6$ etch gases with 5 sccm oxygen addition. In FIG. 16, the positive y-axis represents etch rates while the negative y-axis represents deposition rates; the x-axis represents the compounds compared. FIG. 16 shows that $C_3HF_4N$, $C_2HF_2N$ and $C_5F_5N$ have the infinite selectivity of oxide to nitride with 5 sccm oxygen addition represented as 150.

Comparative Example 5

Figure 17:
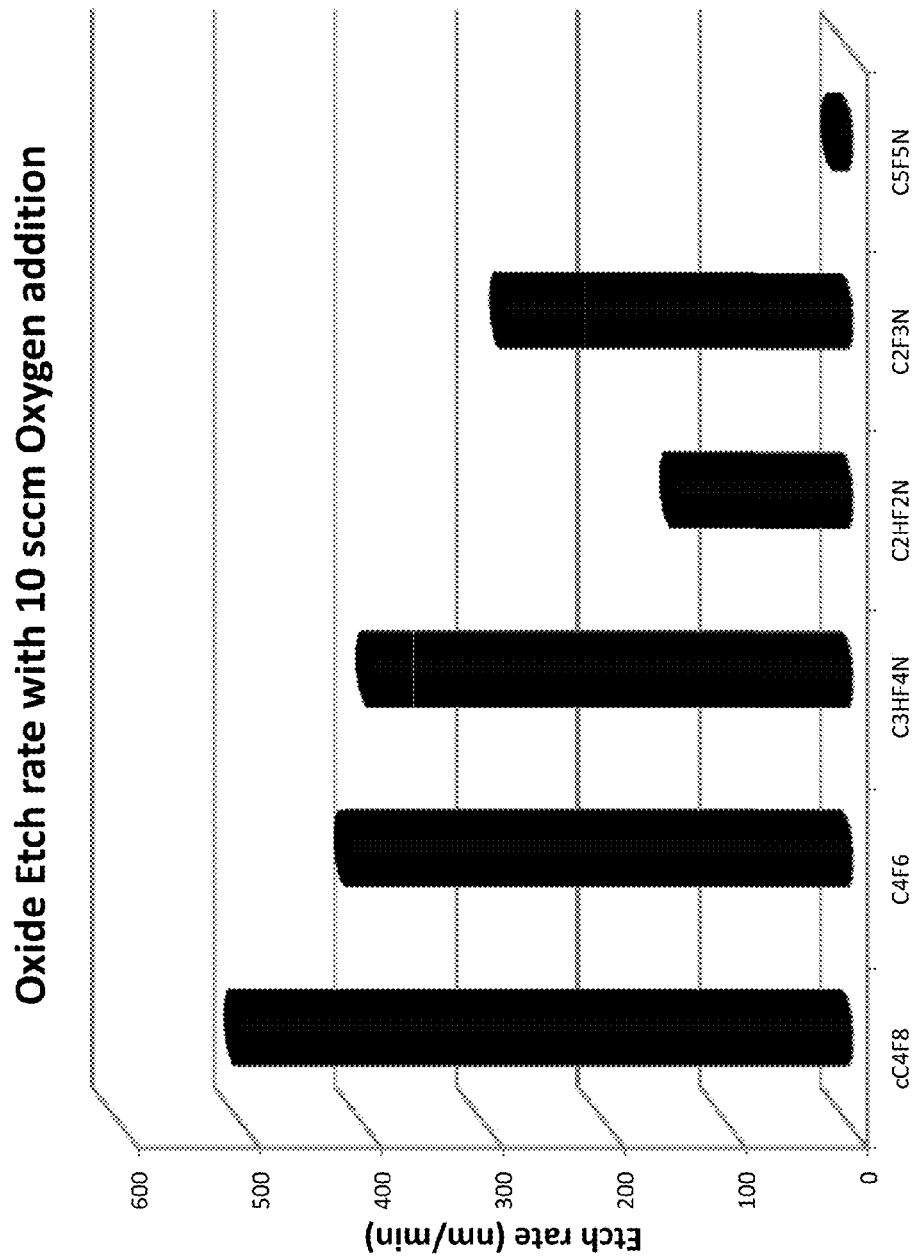
FIG. 17 is a graph comparing the silicon oxide etch rates with 10 sccm oxygen addition of $C_3HF_4N$, $C_2HF_2N$, $C_5F_5N$, and $C_2F_3N$ with $cC_4F_8$ and $C_4F_6$.

FIG. 17 is a graph demonstrating silicon oxide etch rates of $C_3HF_4N$, $C_2HF_2N$, $C_5F_5N$, and $C_2F_3N$ versus the prior art $cC_4F_8$ and $C_4F_6$ etch gases with 10 sccm oxygen addition. In FIG. 17, the positive y-axis represents etch rates while the negative y-axis represents deposition rates; the x-axis represents the compounds compared. As shown in FIG. 17, the rank of the etching rates with 10 sccm oxygen addition are $cC_4F_8 > C_4F_6 > C_3HF_4N > C_2F_3N > C_2HF_2N > C_5F_5N$.

Comparative Example 6

Figure 18:
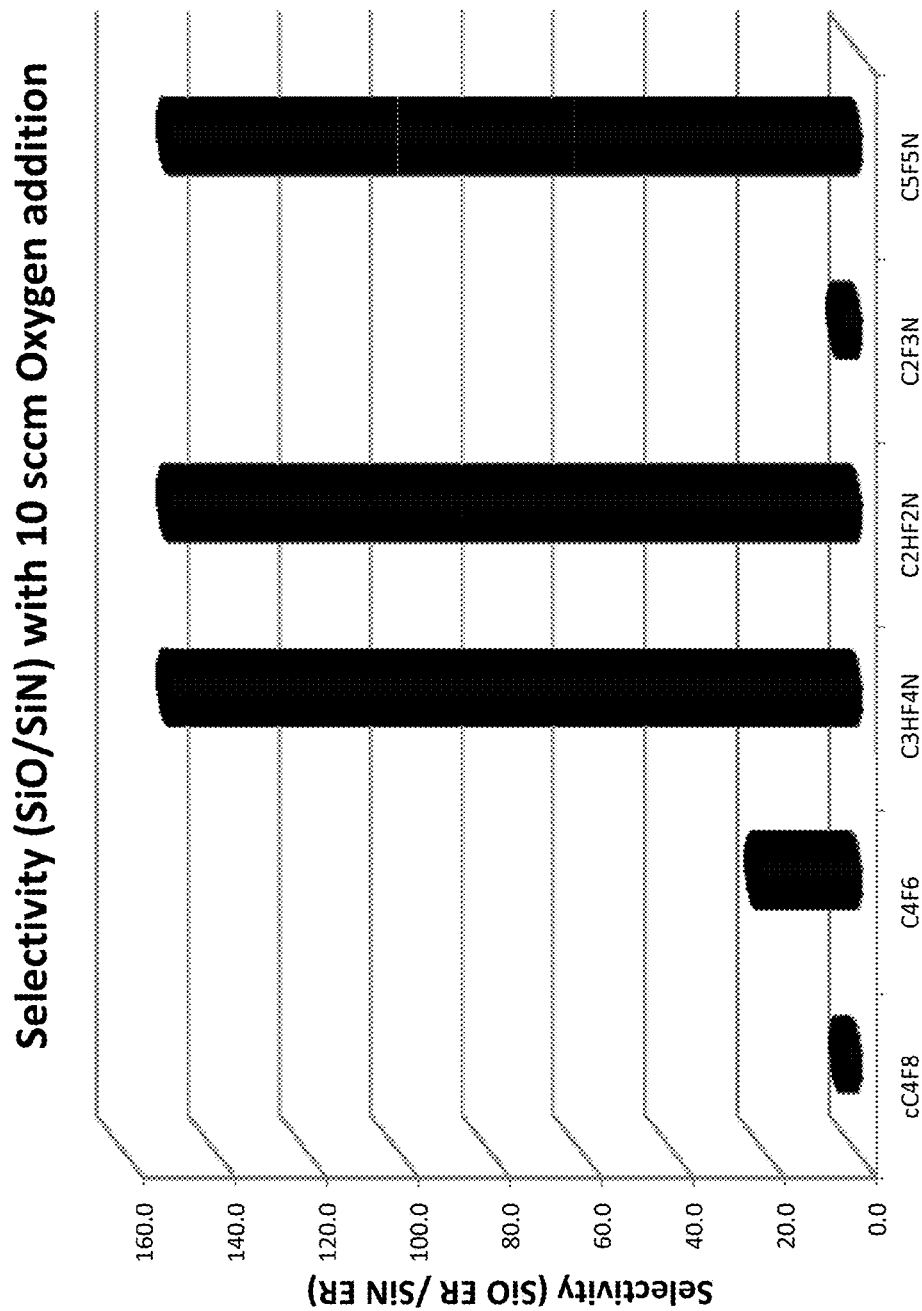
FIG. 18 is a graph comparing the selectivity of silicon oxide to silicon nitride with 10 sccm oxygen addition of $C_3HF_4N$, $C_2HF_2N$, $C_5F_5N$, and $C_2F_3N$ with $cC_4F_8$ and $C_4F_6$.

FIG. 18 is a graph demonstrating selectivity (SiO/SiN) of $C_3HF_4N$, $C_2HF_2N$, $C_5F_5N$, and $C_2F_3N$ versus the prior art $cC_4F_8$ and $C_4F_6$ etch gases with 10 sccm oxygen addition. In FIG. 18, the positive y-axis represents etch rates while the negative y-axis represents deposition rates; the x-axis represents the compounds compared. FIG. 18 shows that $C_3HF_4N$, $C_2HF_2N$ and $C_5F_5N$ have the infinite selectivity of oxide to nitride with 10 sccm oxygen addition represented as 150.

Comparative Example 7

Figure 19:
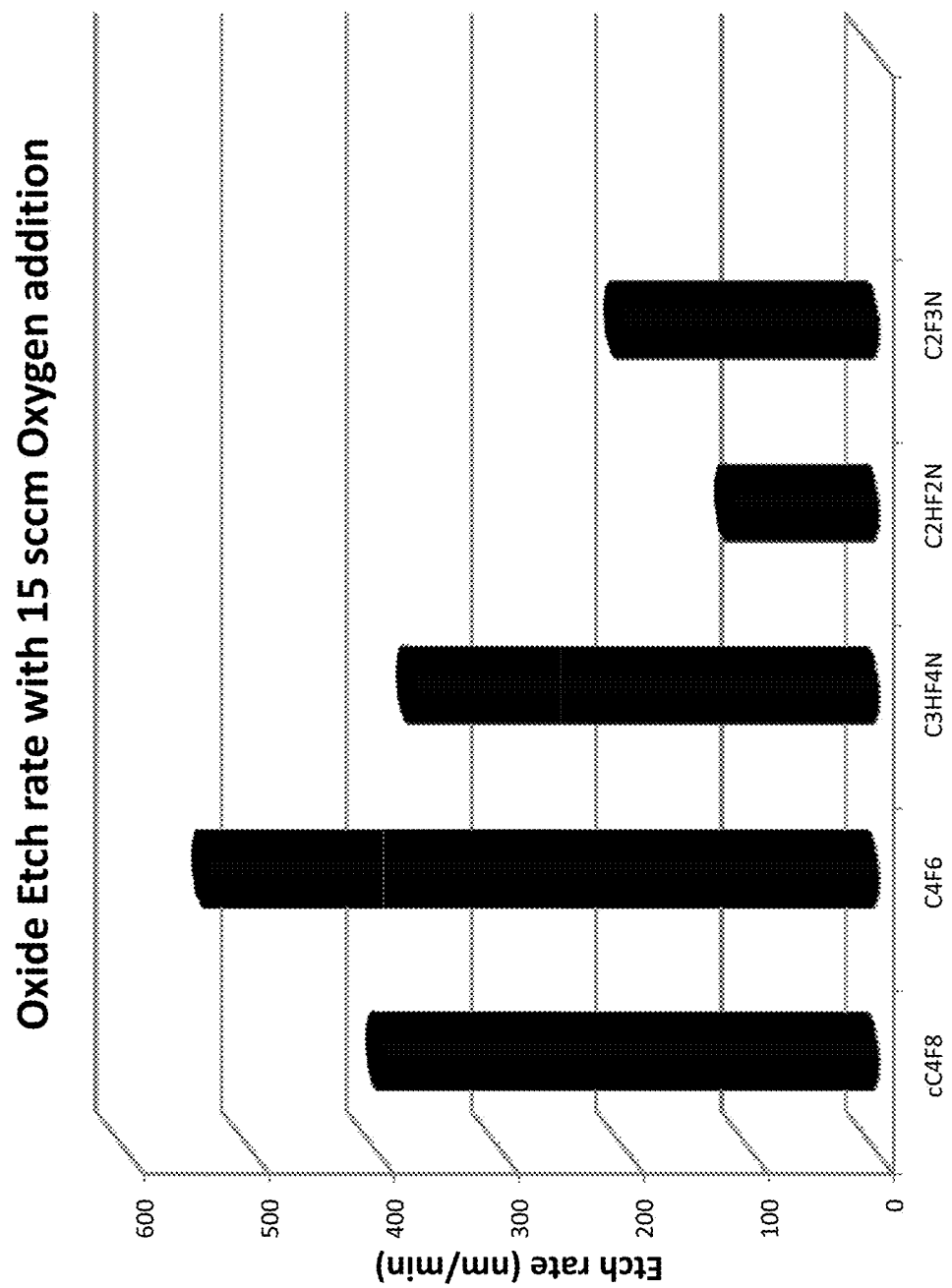
FIG. 19 is a graph comparing the silicon oxide etch rates with 15 sccm oxygen addition of $C_3HF_4N$, $C_2HF_2N$, and $C_2F_3N$ with $cC_4F_8$ and $C_4F_6$.

FIG. 19 is a graph demonstrating silicon oxide etch rates of $C_3HF_4N$, $C_2HF_2N$, and $C_2F_3N$ versus the prior art $cC_4F_8$ and $C_4F_6$ etch gases with 15 sccm oxygen addition. In FIG. 19, the positive y-axis represents etch rates while the negative y-axis represents deposition rates; the x-axis represents the compounds compared. As shown in FIG. 19, the rank of the etching rates with 15 sccm oxygen addition are $C_4F_6 > cC_4F_8 > C_3HF_4N > C_2F_3N > C_2HF_2N$.

Comparative Example 8

Figure 20:
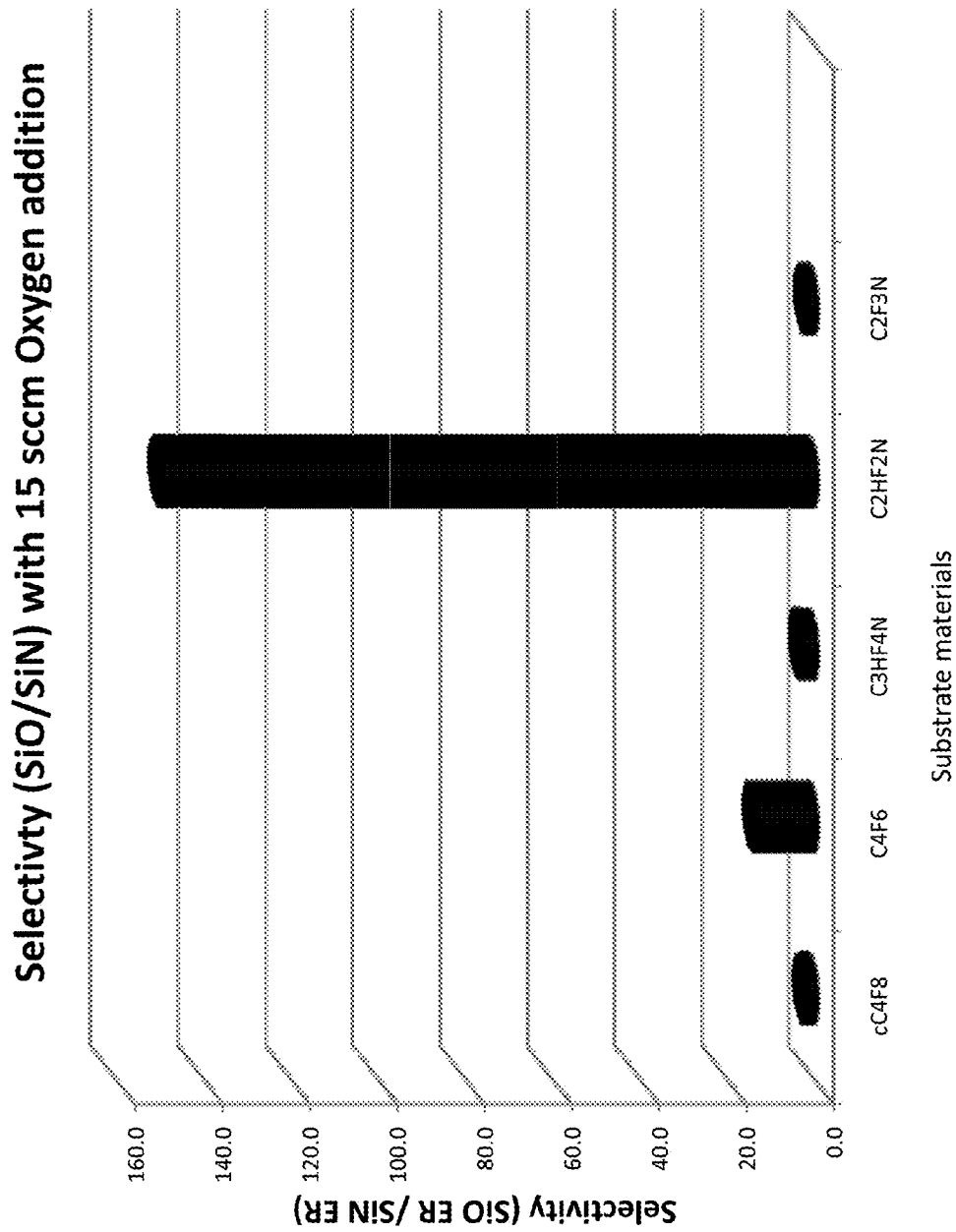
FIG. 20 is a graph comparing the selectivity of silicon oxide to silicon nitride with 15 sccm oxygen addition of $C_3HF_4N$, $C_2HF_2N$, and $C_2F_3N$ with $cC_4F_8$ and $C_4F_6$.

FIG. 20 is a graph demonstrating selectivity (SiO/SiN) of $C_3HF_4N$, $C_2HF_2N$, and $C_2F_3N$ versus the prior art $cC_4F_8$ and $C_4F_6$ etch gases with 15 sccm oxygen addition. In FIG. 20, the positive y-axis represents etch rates while the negative y-axis represents deposition rates; the x-axis represents the compounds compared. FIG. 20 shows that only $C_2HF_2N$ has the infinite selectivity of oxide to nitride with 15 sccm oxygen addition represented as 150.

Comparative Example 9

Figure 21:
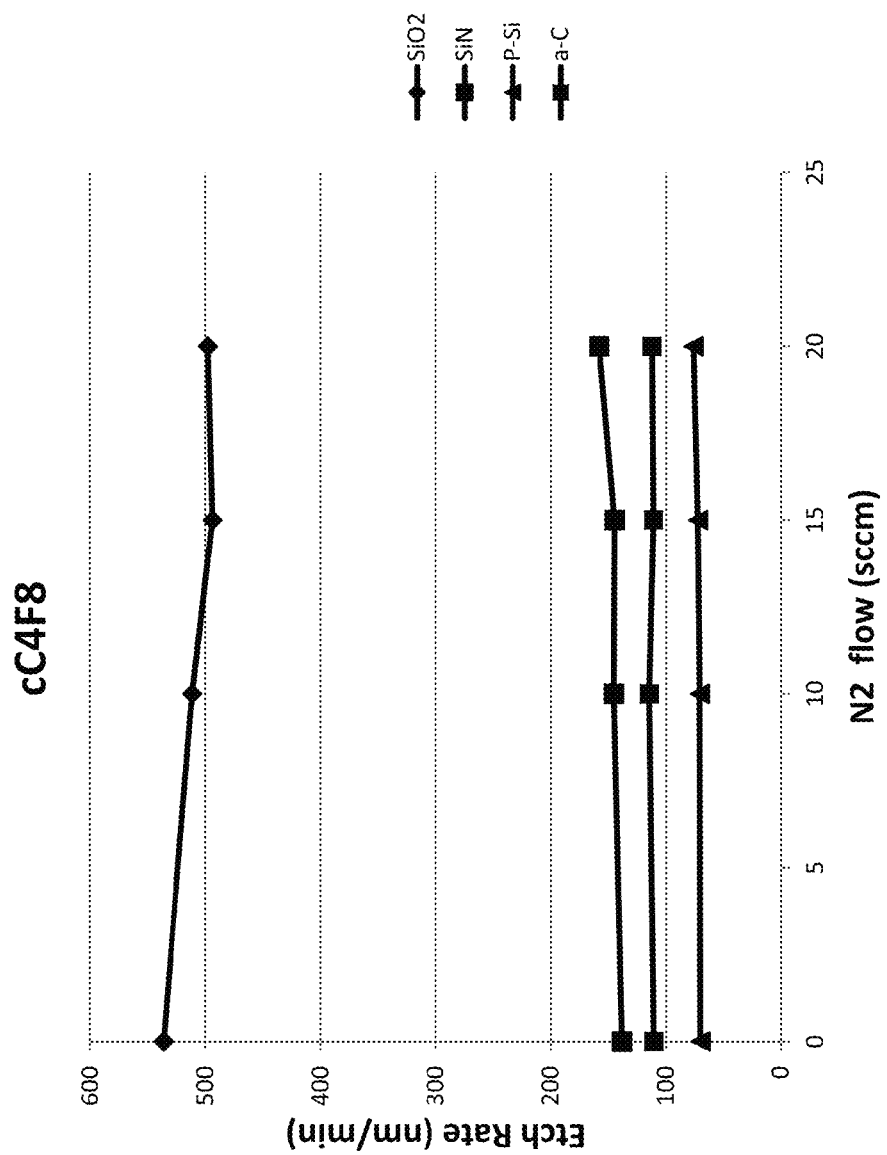
FIG. 21 is a graph demonstrating the effect of adding $N_2$ on etch rates of different substrate materials.

$N_2$ was added to the etch gas mixture (including $cC_4F_8$) to see the effect of $N_2$ on etch rate and selectivity. The etching tests were performed at 30 mTorr, source power of 750 W (27 MHz), and bias power of 1500 W (2 MHz). The feed mixture contained 250 sccm of Ar, 15 sccm of $cC_4F_8$, 10 sccm of $O_2$, while $N_2$ has been varied in the amounts of 0 sccm to 20 sccm. FIG. 21 is a graph demonstrating the effect of adding $N_2$ on etch rates of different substrate materials. In FIG. 21, the positive y-axis represents etch rates while the negative y-axis represents deposition rates; the x-axis represents the $N_2$ flow rate.

As shown, for each substrate (SiO, SiN, p-Si, or a-C), the etch rates varied less than 10% compared to the etch rate when no nitrogen (0 sccm) is added. Thus, nitrogen addition has minimal effect on the etch rates of different substrate materials based on the results shown in FIG. 21.

Comparative Example 10

Figure 22:
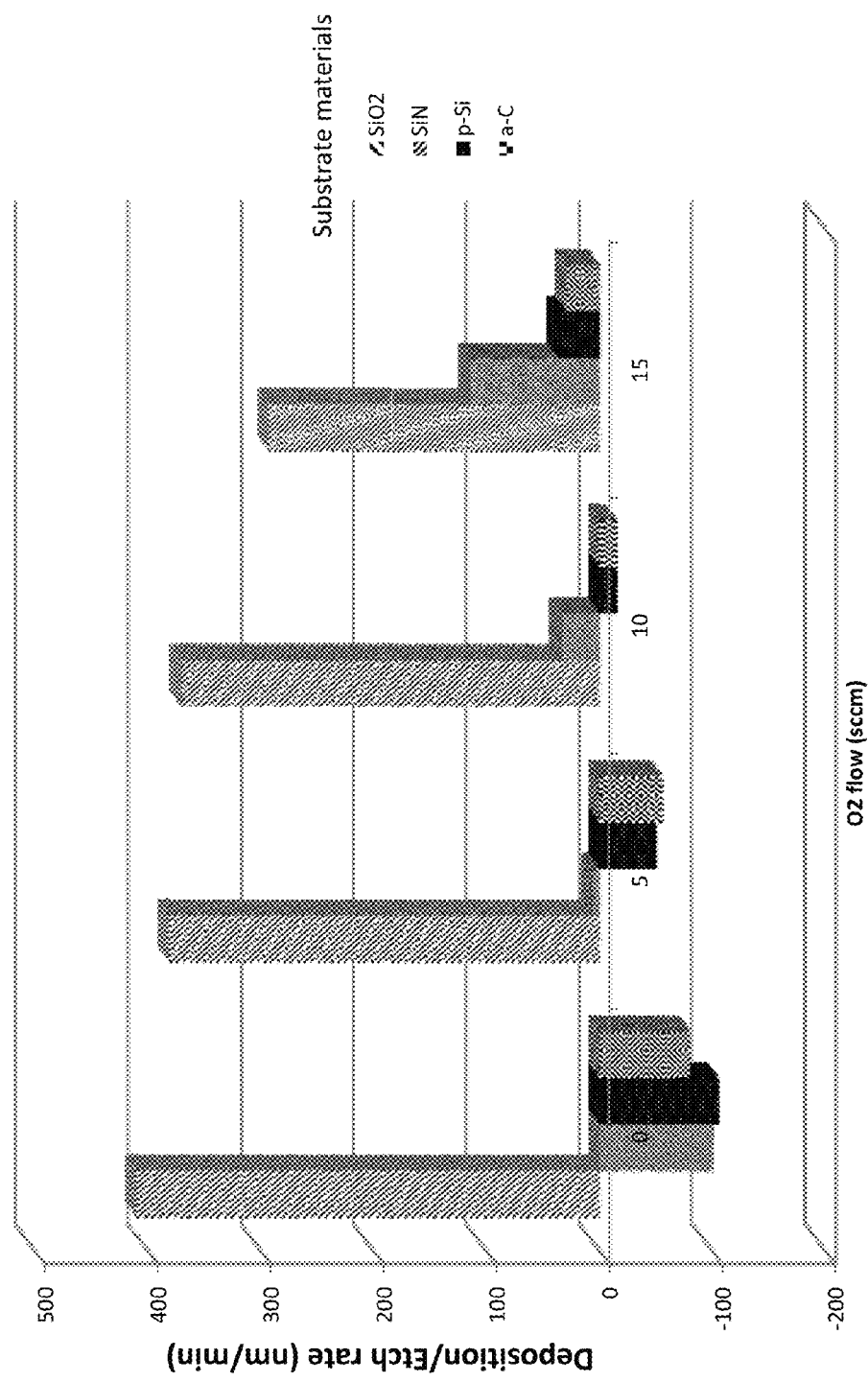
FIG. 22 is a graph demonstrating the effect of adding $O_2$ on the deposition and etch rates of different substrate materials.

$NH_3$ was added to the etch gas mixture to see the effect of nitrogen on etch rate and selectivity. The etching tests were performed at 30 mTorr, source power of 750 W (27 MHz), and bias power of 1500 W (2 MHz). The feed mixture contained 250 sccm of Ar, 15 sccm of $cC_4F_8$, 15 sccm of $NH_3$, while $O_2$ was varied between 0 sccm to 15 sccm. FIG. 22 is a graph demonstrating the effect of adding $O_2$ on etch rates of different substrate materials. In FIG. 22, the positive y-axis represents etch rates while the negative y-axis represents deposition rates; the x-axis represents $O_2$ flow.

As shown, infinite selectivity of silicon oxide to silicon nitride is obtained, when no oxygen is added. However, this condition results in excess polymerization leading to etch stop.

As described above in FIG. 1b, polymer may be deposited on a sidewall during etching. In order to obtain straight etch profiles that are deep, the amount of polymer deposition should be very well controlled. If there is excessive polymerization, it may result in a condition called etch stop phenomenon. To prevent the etch stop, oxygen is often added to the etch gas mixture. However, excess oxygen may result in loss of selectivity. Thus, there is a trade-off between etch stop and selectivity.

As shown in FIG. 22, as oxygen is added, the selectivity decreases. The selectivity of SiO to other materials is significantly better for nitrogen containing organofluororine compounds than by adding Ammonia and varying oxygen flow rates between 5 sccm to 15 sccm (FIGS. 9 and 10). Moreover, the need for another primary organofluororine compound to ammonia in the mixture makes its use difficult for commercial applications.

Deposition tests were performed on 1×1 cm² Si coupon at 30 mTorr, and source power of 750 W (27 MHz), with no bias power. The process feed mixture contained 250 sccm of Ar, 15 sccm of $cC_4F_8$, and 15 sccm of $NH_3$. For these conditions, the deposition rate is found to be 180 nm/min.

Comparative Example 11

Figure 23:
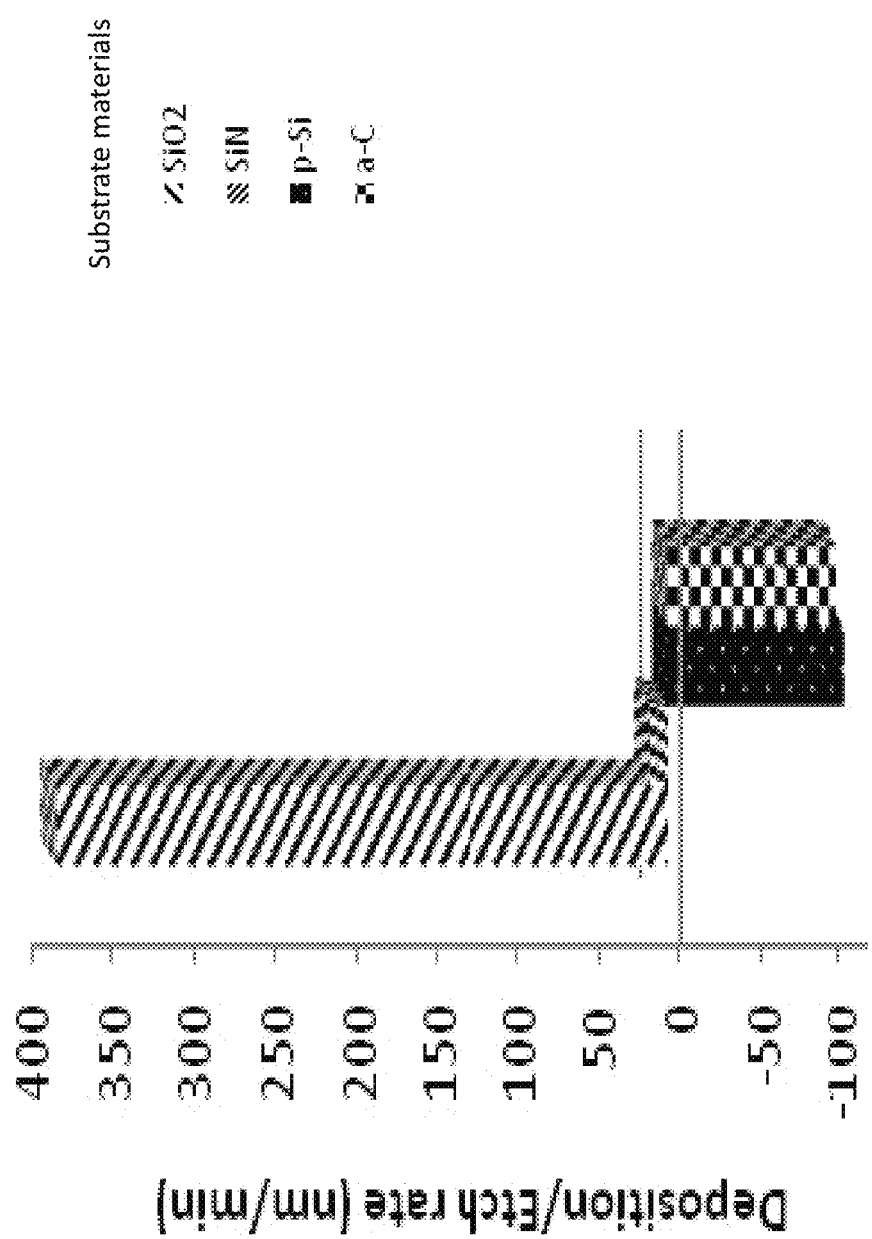
FIG. 23 is a graph demonstrating the deposition and etch rates without oxygen addition of $C_3H_3F_6N$ on different substrate materials.

The prior art R—$NH_2$ etch gas was tested to determine the etch rates of SiO, SiN, p-Si and a-C a function of oxygen flow rate. FIG. 23 is a graph of the results demonstrating etch rates without oxygen addition of $C_3H_3F_6N$ (1,1,1,3,3,3-hexafluoroisopropylamine,

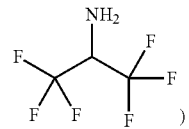

)

on different substrate materials. For the deposition test conditions, it deposits at 210 nm/min and so may offer sidewall protection. This molecule offers good selectivity to p-Si and a-C but loses selectivity to SiN film even without any oxygen addition.

Comparative Example 12

Figure 24:
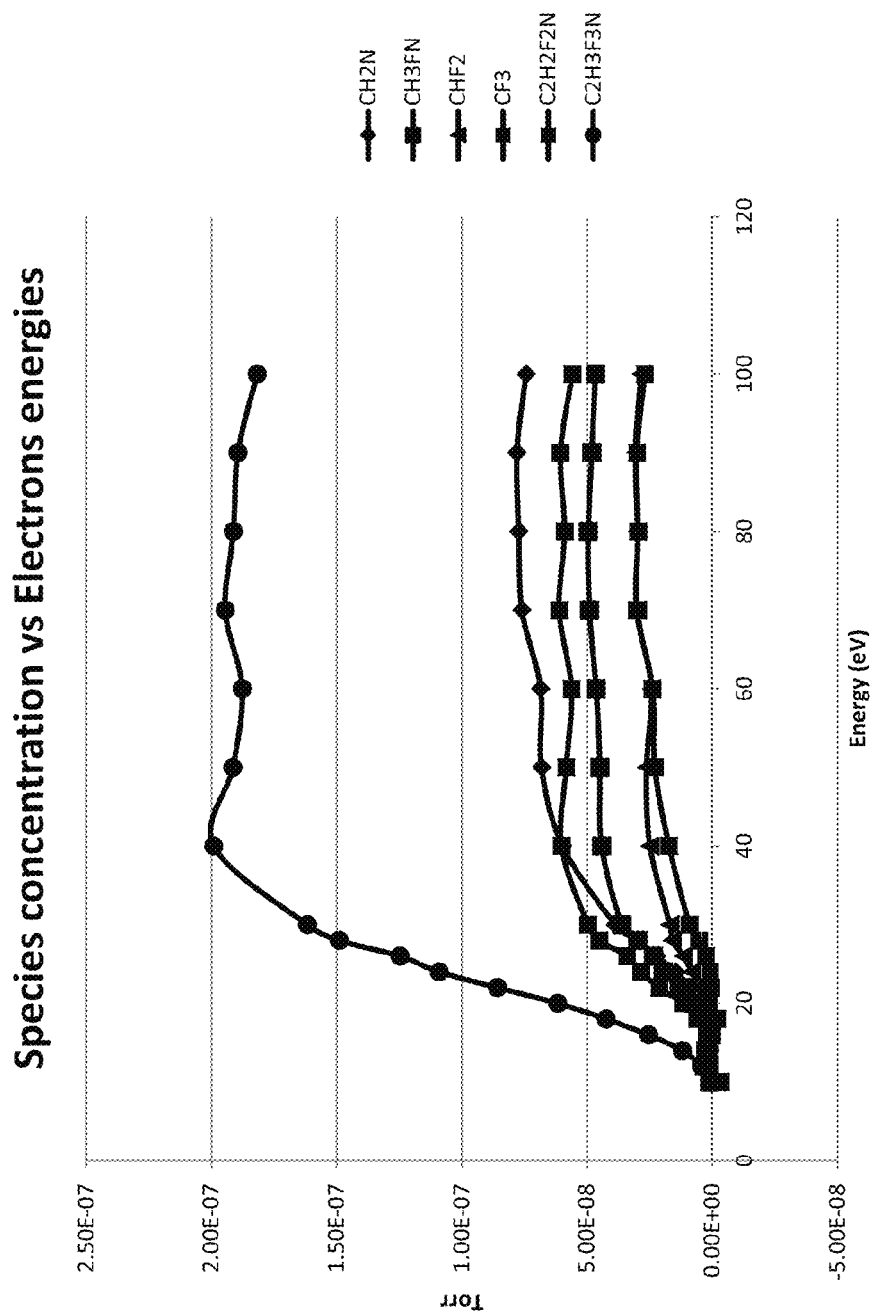
FIG. 24 is a graph demonstrating the electron impact ionization data versus energy for $C_3H_3F_6N$.

FIG. 24 is a graph demonstrating electron impact ionization data for $C_3H_3F_6N$. In FIG. 24, the x-axis represents electron energy and y-axis represents the partial pressure of the fragment species. FIG. 24 shows that the major fragments for $C_3H_3F_6N$ is $C_2H_3F_3N$. The $C_2H_3F_3N$ fragment has high F/C ratio and may not provide etch resistance polymers on the substrate.

In summary, the evaluation of the dry etching of SiO, SiN, p-Si and a-C films with nitrogen containing organofluorine compound plasmas shows that the nitrogen containing HFCs yield highest (up to infinite) selectivity of silicon oxide to silicon nitride, and p-Si than the prior art fluorocarbons. The reason for high selectivity may be attributed to the formation of low F/C nitrogen containing fragments during plasma dissociation of the etch gases, which results in the formation of a protective polymer film on the substrates. The polymer film, when analyzed with XPS, shows the evidence of C, F, and N. The resulting film has the formula $CF_xN_y$, wherein x, y=0.01 to 5. The presence of nitrogen in the polymerizing film offers an extra layer of protection in comparison to the standard $cC_4F_8$ gas where only a $CF_x$ type polymer is formed, wherein x=0.01 to 5. The etching gas results presented herein show they are not only ready for contact etch process, but also may be beneficial for other etching processes on silicon or metal containing substrates.

While embodiments of this invention have been shown and described, modifications thereof may be made by one skilled in the art without departing from the spirit or teaching of this invention. The embodiments described herein are exemplary only and not limiting. Many variations and modifications of the composition and method are possible and within the scope of the invention. Accordingly the scope of protection is not limited to the embodiments described herein, but is only limited by the claims which follow, the scope of which shall include all equivalents of the subject matter of the claims.

What is claimed is:

1. A method for etching silicon-containing films, the method comprising the steps of:
   introducing a vapor of a nitrogen containing etching compound into a reaction chamber containing a silicon-containing film on a substrate, wherein the nitrogen containing etching compound comprises an organofluorine compound having a formula selected from the group consisting of N≡C—R¹, wherein R¹ has the formula $H_aF_bC_c$ and a=1-11, b=1-11, and c=1-5; (N≡C—)—(R²)—(—C≡N), wherein R² has the formula $H_aF_bC_c$ with a=0, b=1-11, and c=1-5; and $R^1_x$[—C≡N($R^2_z$)]$_y$, wherein x=1-2, y=1-2, z=0-1, x+z=1-3, and each $R^1$ and $R^2$ independently has the formula $H_aF_bC_c$ with a=0-11, b=0-11, and c=0-5;

introducing an inert gas into the reaction chamber; and activating a plasma to produce an activated nitrogen containing etching compound capable of etching the silicon-containing film from the substrate;

wherein the nitrogen containing etching compound having a purity ranging from approximately 95% to approximately 99.999% by volume and comprising between approximately 10 parts per trillion to approximately 5% by volume water vapor impurities.

2. The method of claim 1, further comprising removing volatile by-products from the reaction chamber, wherein the activated nitrogen containing etching compound reacts with the silicon-containing film to form the volatile by-products.

3. The method of claim 2, wherein the organofluorine compound containing the C≡N functional group has the formula: N≡C—$R^1$ or (N≡C—)—($R^1$)—(—C≡N), wherein each $R^1$ is independently a functional group having the formula $H_aF_bC_c$ with a=0-11, b=1-11, and c=0-5.

4. The method of claim 2, wherein the organofluorine compound containing the C≡N functional groups has the formula: $R^1_x$[—C≡N($R^2_z$)]$_y$, wherein x=1-2, y=1-2, z=0-1, x+z=1-3, and each $R^1$ and $R^2$ independently has the formula $H_aF_bC_c$ with a=0-11, b=0-11, and c=0-5.

5. The method of claim 1, wherein the organofluorine compound is selected from the group consisting of 2,2,3,3-tetrafluoropropionitrile, 2,3,3,3-tetrafluoropropionitrile ($C_3HF_4N$), difluoroacetonitrile ($C_2HF_2N$), Hexafluoroacetone imine ($C_3HF_6N$), 4,4,4-Trifluorocrotono-nitrile, 3,3,3-Trifluoropropionitrile, fluoroacetonitrile, octafluorohexane-1,6-dinitrile, 1,1-bis(trifluoromethyl)-2,2-dicyanoethylene, N,1,1,1,3,3,3-heptafluoro-propanamine, and 1,1,1,6,6,6-Hexafluoro-3-azahex-3-ene.

6. The method of claim 1, wherein the organofluorine compound is 2,3,3,3-tetrafluoropropionitrile ($C_3HF_4N$).

7. The method of claim 1, wherein the organofluorine compound is difluoroacetonitrile ($C_2HF_2N$).

8. The method of claim 1, wherein the inert gas is selected from the group consisting of He, Ar, Xe, Kr, Ne and $N_2$.

9. The method of claim 8, wherein the inert gas comprises approximately 0.01% v/v to approximately 99.9% v/v of a total volume of the vapor of the nitrogen containing etching compound and the inert gas introduced into the reaction chamber.

10. The method of claim 1, further comprising introducing an oxidizer into the reaction chamber.

11. The method of claim 10, wherein the oxidizer is selected from the group consisting of $O_2$, CO, $CO_2$, NO, $N_2O$, COS and $NO_2$.

12. The method of claim 10, wherein the oxidizer comprises approximately 0.01% v/v to approximately 99.99% v/v of a total volume of the vapor of the nitrogen containing etching compound and the oxidizer introduced into the reaction chamber.

13. The method of claim 1, wherein the silicon-containing film comprises a layer of silicon oxide, silicon nitride, polysilicon, crystalline silicon, low-k SiCOH, SiOCN, SiON, $Si_aO_bH_cC_dN_e$, where a>0; b, c, d and e≥0, or combinations thereof.

14. The method of claim 13, wherein the silicon-containing film is selectively etched from an amorphous carbon layer or a photoresist layer.

15. The method of claim 13, wherein the silicon oxide layer is selectively etched from a silicon nitride, polysilicon or amorphous carbon layer.

16. The method of claim 2, wherein the method produces an aperture in the silicon-containing film having an aspect ratio between approximately 10:1 and approximately 200:1.

17. The method of claim 1, further comprising improving selectivity by introducing an etch gas into the reaction chamber, wherein the etch gas is selected from the group consisting of $cC_4F_8$, $C_4F_8$, $C_4F_6$, $C_5F_8$, $CF_4$, $CH_3F$, $CF_3H$, $CH_2F_2$, COS, $CS_2$, $CF_3I$, $C_2F_3I$, $C_2F_5I$, F—C≡N, $SO_2$, trans-1,1,1,4,4,4-hexafluoro-2-butene (trans-$C_4H_2F_6$), cis-1,1,1,4,4,4-hexafluoro-2-butene (cis-$C_4H_2F_6$), hexafluoroisobutene ($C_4H_2F_6$), trans-1,1,2,2,3,4-hexafluorocyclobutane (trans-$C_4H_2F_6$), 1,1,2,2,3-pentafluorocyclobutane ($C_4H_3F_5$), 1,1,2,2-tetrafluorocyclobutane ($C_4H_4F_4$), cis-1,1,2,2,3,4-hexafluorocyclobutane (cis-$C_4H_2F_6$), and combinations thereof.

18. A nitrogen containing etching compound having a purity ranging from approximately 95% to approximately 99.999% by volume and comprising between approximately 10 parts per trillion to approximately 5% by volume water vapor impurities, the nitrogen containing etching compound comprising an organofluorine compound selected from the group consisting of difluoroacetonitrile, 2,3,3,3-tetrafluoropropionitrile, 2,2,3,3-tetrafluoropropionitrile, hexafluoroacetone imine, 4,4,4-Trifluorocrotono-nitrile, 3,3,3-Trifluoropropionitrile, fluoroacetonitrile, octafluorohexane-1,6-dinitrile, 1,1-bis(trifluoromethyl)-2,2-dicyanoethylene, N,1,1,3,3,3-heptafluoro-propanamine, and 1,1,1,6,6,6-Hexafluoro-3-azahex-3-ene.

19. A method for selectively etching silicon oxide films from a substrate selected from silicon nitride, amorphous carbon, polysilicon, or combinations thereof, the method comprising the steps of:

introducing a vapor of a nitrogen containing etching compound into a reaction chamber containing a silicon oxide film on a substrate selected from silicon nitride, amorphous carbon, polysilicon, or combinations thereof, wherein the nitrogen containing etching compound comprises an organofluorine compound having a formula selected from of N≡C—$R^1$, wherein $R^1$ has the formula $H_aF_bC_c$ and a=1-11, b=1-11, and c=1-5 or (N≡C—)—($R^2$)—(—C≡N), wherein $R^2$ has the formula $H_aF_bC_c$ with a=0, b=1-11, and c=1-5;

introducing an inert gas into the reaction chamber; and activating a plasma to produce an activated nitrogen containing etching compound that etches the silicon oxide film from the substrate selected from silicon nitride, amorphous carbon, polysilicon, or combinations thereof;

wherein the nitrogen containing etching compound having a purity ranging from approximately 95% to approximately 99.999% by volume and comprising between approximately 10 parts per trillion to approximately 5% by volume water vapor impurities.

20. The method of claim 19, wherein the organofluorine compound is 2,3,3,3-tetrafluoropropionitrile ($C_3HF_4N$) or difluoroacetonitrile ($C_2HF_2N$).

* * * * *